US008567410B2

(12) United States Patent
Rudolph et al.

(10) Patent No.: US 8,567,410 B2
(45) Date of Patent: Oct. 29, 2013

(54) MAGNET-FIELD CONTROLLED ACTIVE SUBSTANCE TRANSFER FOR AEROSOL THERAPY

(75) Inventors: Carsten Rudolph, Munich (DE); Joseph Rosenecker, Munsing (DE)

(73) Assignee: Ethris GmbH (DE)

( * ) Notice: Subject to any disclaimer, the term of this patent is extended or adjusted under 35 U.S.C. 154(b) by 729 days.

(21) Appl. No.: 11/991,535

(22) PCT Filed: Aug. 25, 2006

(86) PCT No.: PCT/EP2006/008357
§ 371 (c)(1),
(2), (4) Date: Jul. 2, 2009

(87) PCT Pub. No.: WO2007/028512
PCT Pub. Date: Mar. 15, 2007

(65) Prior Publication Data
US 2009/0299127 A1   Dec. 3, 2009

(30) Foreign Application Priority Data

Sep. 8, 2005   (DE) .......................... 10 2005 042 768

(51) Int. Cl.
*A61B 19/00*   (2006.01)
(52) U.S. Cl.
USPC ...... 128/899; 128/897; 128/203.12; 424/450; 514/769; 514/44 R; 977/700; 977/773; 977/838; 977/960; 977/962; 977/963; 623/1.46; 600/1; 600/2; 600/3; 600/4; 600/5; 600/6; 600/7; 600/8; 600/9; 600/10; 600/11; 600/12; 600/13; 600/14; 600/15; 604/891.1

(58) Field of Classification Search
USPC ........ 600/1–15; 128/203.12, 899, 897; 514/2, 514/44 R, 769; 424/450; 977/700, 773, 838, 977/960, 962, 963; 604/891.1; 623/1.46
See application file for complete search history.

(56) References Cited

U.S. PATENT DOCUMENTS

| | | | |
|---|---|---|---|
| 2002/0086842 A1* | 7/2002 | Plank et al. ..................... 514/44 |
| 2004/0096511 A1* | 5/2004 | Harburn et al. ............... 424/489 |
| 2005/0147654 A1 | 7/2005 | Matloub et al. | |
| 2006/0142632 A1* | 6/2006 | Meretei .......................... 600/12 |
| 2006/0165805 A1* | 7/2006 | Steinhoff et al. ............. 424/489 |

FOREIGN PATENT DOCUMENTS

| | | |
|---|---|---|
| DE | 10020376 | 8/2001 |
| WO | WO03026618 | 4/2003 |
| WO | WO 2004/108165 | 12/2004 |

(Continued)

OTHER PUBLICATIONS

Effect of gravity on aerosol dispersion and deposition in the human lung after periods of breath holding. Chantal Darquenne, Manuel Paiva and G. Kim Prisk.J Appl Physiol 89:1787-1792, 2000.*

(Continued)

*Primary Examiner* — Christine Matthews
*Assistant Examiner* — Sunita Reddy
(74) *Attorney, Agent, or Firm* — McDonnell Boehnen Hulbert & Berghoff LLP

(57) ABSTRACT

The present invention relates to aerosols containing magnetic particles, wherein the aerosols comprise magnetic particles and a pharmaceutical active agent. The invention furthermore relates to the use of such aerosols containing magnetic particles for directed magnetic field-guided transfer of the active agents contained therein in aerosol therapy.

28 Claims, 22 Drawing Sheets

Figure 1:
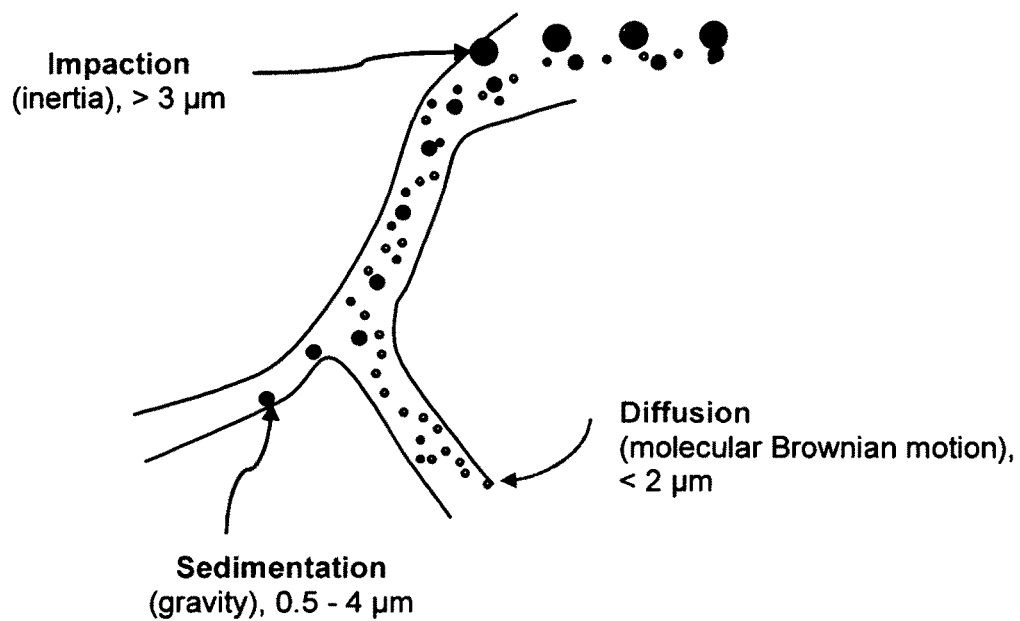

Concept of magnetic field-guided administration of aerosol

(56) References Cited

FOREIGN PATENT DOCUMENTS

| WO | WO 2004/112799 | 12/2004 |
|---|---|---|
| WO | WO2004108165 | 12/2004 |
| WO | WO2004112799 | 12/2004 |
| WO | WO2005013897 | 2/2005 |

OTHER PUBLICATIONS

Gene Therapy in Lung Transplantation: Effective Gene Transfer via The Airways. Anders Jeppsson, Ronald Lee, Carlo Pellegrini, Timothy O'Brien, Henry D. Tazelaar and Christopher G. McGregor. J Thorac Cardiovasc Surg 1998;115:638-643.*

Dendritic cells transduced with an adenovirus vector encoding interleukin-12 are a potent vaccine for invasive pulmonary aspergillosis. C Shao, J Qu, L He, Y Zhang, J Wang, H Zhou, Y Wang2 and X Liu. Genes and Immunity (2005) 6, 103-114. Published online Jan. 27, 2005.*

The magnetofection method: using magnetic force to enhance gene delivery. Plank C, Schillinger U, Scherer F, et al, May 2003, Biol. Chem. 384 (5): 737-47.*

Ally, J., et al.: "Magnetic Targeting of Aerosol Particles for Cancer Therapy", Journal of Magnetism and Magnetic Materials, vol. 293, pp. 442-449, 2005.

Dikanskii, Y.I., et al.: "Magnetosensitive Aerosols and Prospects of Their Application", Magnetohydrodynamics, vol. 34(3), pp. 212-215, 1998.

Ally, J., et al.: "Magnetic Targeting of Aerosol Particles for Cancer Therapy," Journal of Magnetism and Magnetic Materials, vol. 293, pp. 442-449, 2005.

Dikanskii, Yu I., et al.: "Magnetosensitive Aerosols and Prospects of Their Application," Magnetohydrodynamics, vol. 34(3), pp. 212-215, 1998.

Bennet, W.D., et al.: "Targeting Delivery of Aerosols to Different Lung Regions," Journal of Aerosol Medicine, vol. 15(2), 2002, pp. 179-188.

* cited by examiner

Diagram of the deposition mechanisms as a function of the particle diameter

Deposition of particles in the lung

Deposition of particles in the lung

Lung, dorsal

Deposition pattern of conventionally administered aerosols in the lung

Figure 4

Demonstration of cells from the mucus layer of the lung with (A) and without (B) magnetic particle deposition Concept of magnetic field-guided administration of aerosol

Figure 7

Diagram of the set-up of the animal study on magnetic field-guided administration of aerosol

Figure 8

Set-up of the animal study on magnetic field-guided administration of aerosol

Figure 9

Histological evaluation of the animal study on the magnetic field-guided administration of aerosol

Figure 10

Quantitative evaluation of the animal study on the magnetic field-guided administration of aerosol; thorax opened, electromagnet placed on the right lung

Figure 11

Quantitative evaluation of the animal study on the magnetic field-guided administration of aerosol; thorax closed, electromagnet placed on the right lung

Figure 12

Diagram of the study set-up for investigating the magnetic field-induced deflection of the aerosol Ø = 7 mm
$v_{air}$ = 4.76 m/s

Figure 14

Figure 15

Magnetic field-induced aerosol deflection of aerosols containing superparamagnetic iron oxide particles

Figure 16

Influence of the parameter of field strength (T) on the aerosol deflection (cm)

Figure 17

Influence of the parameter of magnetic particle diameter [d (nm)] on the aerosol deflection [A (cm²)]

Figure 18

Influence of the parameter of iron concentration [c (mg/ml)] on the aerosol deflection [A (cm$^2$)]

Figure 19

| Field strength (mT) | Relative deposition rate (%) | Decrease compared with a concentration of 25 mg/ml |
|---|---|---|
| 1000 | 100 | - |
| 870 | 76 | 1.3-fold |
| 730 | 68 | 1.5-fold |

Results of Figure 17 in tabular form

| Magnetic particle diameter (nm) | Relative deposition rate (%) | Decrease compared with a diameter of 50 nm |
|---|---|---|
| 50 | 100 | - |
| 100 | 80 | 1.25-fold |
| 400 | 81 | 1.23-fold |
| 1000 | 0 | > 100-fold |
| 2000 | 0 | > 100-fold |

Results of Figure 18 in tabular form

| Ion concentration (mg/ml) | Relative deposition rate (%) | Decrease compared with a concentration of 25 mg/ml |
|---|---|---|
| 50.0 | 88 | 1.14-fold |
| 25.0 | 100 | - |
| 12.5 | 5 | 19-fold |
| 6.3 | 0 | > 100-fold |
| 3.1 | 0 | > 100-fold |
| 1.6 | 0 | > 100-fold |
| 0.8 | 0 | > 100-fold |

Results of Figure 19 in tabular form

Figure 20

MAGNET-FIELD CONTROLLED ACTIVE SUBSTANCE TRANSFER FOR AEROSOL THERAPY

This application is a U.S. national stage application under 35 U.S.C. §371 of PCT International Application Number PCT/EP2006/008357, filed on Aug. 25, 2006, which claims the benefit of German application number 10 2005 042 768.5, filed Sep. 8, 2005.

The present invention relates to aerosols containing magnetic particles, wherein the aerosols comprise magnetic particles and a pharmaceutical active agent. The invention furthermore relates to the use of such aerosols containing magnetic particles for directed magnetic field-guided transfer of the active agents contained therein in aerosol therapy.

Aerosols are solid or liquid suspended particles in gases (in particular air) having a diameter of from about 0.0001 μm to about 100 μm, it being possible for the composition and form of aerosols to vary very greatly. If solid particles are present in the aerosol, such aerosols are typically called smokes or dusts, whereas if liquid particles are present in the aerosol, these aerosols are typically called mists. In addition, mixed forms of these aerosols can also occur, i.e. aerosols with solid and liquid suspended particles. In recent decades numerous synthetic aerosols have been prepared for a wide industrial and commercial field of use. Such synthetic aerosols can be prepared by conventional dispersion and condensation processes and are as a rule used in spray cans in combination with a liquefied compressed gas as the propellant gas. Depending on the nature of the particles contained therein, they are used, for example, as hair and body care compositions, deodoránts, perfumes, odour improvers, disinfection and pest control compositions, flooring, glass and furniture care compositions, lacquers and paints, automobile care compositions etc. Aerosols are also used in particular, with and without propellant gas, in the field of medicine, in so-called aerosol therapy for treatment of various diseases of the respiratory tract and/or lungs. Pharmaceutical active agents, e.g. salbutamol, formoterol, ipatropium bromide, budesonide, fenoterol, terbutaline, tiotropium bromide, salmeterol, beclometasone, fluticasone, mometasone, tobramycin, theophylline, dornase $\alpha,\alpha_1$-antitrypsin, interferon-$\beta$, insulin, calcitonin or growth hormones, can be administered via the lungs by means of the medicinal aerosols mentioned last. The present invention and following description relate to such medicinal aerosols.

The smallest (pharmaceutically active) particles in medicinal aerosols are e.g. nucleic acids, peptides or proteins, while the largest particles are e.g. mist particles. The aerosols often comprise mixtures of particles of different particles sizes and therefore embody a polydisperse size distribution. When considering the size distribution of aerosols, it is generally important whether the number, the surface or the weight of the particles is under consideration (it being noted in this connection that, for example, a particle of diameter 10 μm corresponds to the weight of 1,000 particles of diameter 1 μm). The size distribution spectrum is generally specified by a parameter called the mass median aerodynamic diameter (MMAD), as a rule 50% of the aerosol mass being larger and 50% smaller than the MMAD. In this connection, it is to be noted that for biological systems in particular, the mass aerodynamic distribution of the aerosol spectrum is as a rule used, such as is described, for example, by Köhler, D. & Fischer, F. in *Theorie und Praxis der Inhalationstherapie [Theory and Practice of Inhalation therapy]* (Arcis Verlag GmbH, Munich, 2000).

Medicinal aerosols in aerosol therapy are typically inhaled orally or nasally by the patient to be treated. During or after inhalation of the particles into the lung a certain proportion of the particles escapes from the flow line of the particles formed by the in- or exhalation and thereby comes into contact with the moist surface of the air cavities, e.g. the throat, nasal or pharyngeal cavity, the trachea or the lung tissue. This phenomenon is in general called particle deposition or deposition and is subject in particular to the following three physical mechanisms:
  impaction,
  sedimentation and
  diffusion In impaction, the aerosol particles up to a certain diameter follow the flow line of the inhaled aerosol. Above a diameter of from 2 to 3 μm, the inertia of the aerosol becomes relevant, which means that the aerosol particles have the tendency to fly straight on when the flow line of the aerosol changes direction, and to be deposited on the surface. Such changes in direction of the flow line of the aerosol take place in particular due to the physiological shape of the respiratory tracts, e.g. the oropharynx, the branchings of the respiratory tract to the left and right lung lobe and/or the branchings in the region of the alveoli. The deposition probability (DE) for impaction is proportional to the square of the diameter (d) and the aerosol flow (V):

$$DE \sim d^2 \cdot V$$

Impaction is an important deposition mechanism for aerosols in the size range above a particle diameter of 3 μm. Deposition by impaction is therefore to be found everywhere where high aerosol speeds and marked changes in direction occur, as is mostly the case in the wide respiratory tract and the oropharynx. Larger particles above 10 μm are deposited above all to the extent of more than 90% at the first marked change in direction, i.e. the oropharynx (see e.g. Köhler, D. & Fischer (2000, supra); Schulz, H. & Muhle, H. 323-345 (Academic Press, 2000)).

Sedimentation is a deposition mechanism which is to be attributed to the gravity of the aerosol particles. Here also, deposition depends on the particle size and takes place in particular at a particle diameter above from 0.5 to 1 μm. The settling speed ($v_s$), which is the determining factor here, can be described approximately by the following equation:

$$V_s = \frac{d^2 \cdot g \cdot \rho}{18 \cdot \eta}$$

The settling speed ($v_s$) depends on the square of the particle diameter (d), the gravity constant (g), the particle density ($\rho$) and the viscosity ($\eta$) of the gas (see e.g. Köhler, D. & Fischer (2000, supra)).

In contrast to impaction and sedimentation, in diffusion, particles having a diameter of smaller than 1 μm on the one hand still follow the gas stream, i.e. the flow line, and on the other hand more and more resemble molecules which are subjected to molecular Brownian motion. Due to diffusion, in the vicinity of the wall these particles can therefore leave their initial flow line and be deposited on the wall. The average advancement of a particle ($\Delta$) during diffusion is calculated as follows:

$$\Delta = \sqrt{\frac{2 \cdot k \cdot T \cdot C \cdot t}{\pi \cdot \eta \cdot d}}$$

The average advancement of a particle (Δ) during diffusion therefore depends on the particle diameter (d), the viscosity of the gas (η), the time (t) and the temperature (T in ° K.). The constants of the equation are: C=Cunningham's slip correction and k=Boltzmann constant. The diffusion distance somewhat resembles a bell-shaped frequency distribution around the starting value, the average advancement being proportional to the root of the variable (see e.g. Köhler, D. & Fischer (2000, supra)).

Table 1 gives a comparative overview of the distances covered with respect to sedimentation and diffusion. It can be seen that small particles can cover considerable distances via diffusion.

TABLE 1

Sedimentation and diffusion distances of 6 different particle diameters (see e.g. Köhler, D. & Fischer (2000, supra)).

| Particle diameter [μm] | Sedimentation [μm/s] | Diffusion [μm/s] |
|---|---|---|
| 0.01 | 0.07 | 340 |
| 0.1 | 0.7 | 38 |
| 1 | 38 | 8 |
| 5 | 740 | 3 |
| 10 | 2,910 | 2 |
| 100 | 72,000 | 1 |

For therapeutic use of aerosols, the deposition mechanism is of decisive importance for the choice of the particle size of various active agents for therapy and/or prophylaxis of diverse diseases of the respiratory tract and/or lungs. In addition, however, the matter of the regions in which the inhaled particles are to be deposited in the lung is of considerable importance. Detailed studies in the prior art have shown that under certain circumstances (e.g. the particle size described above or the breathing technique, i.e. the nature and manner of breathing) deposition takes place preferentially in certain compartments of the bronchial tree or alveolar region. For effective and gentle therapy it is desirable for the aerosols and the pharmaceutical active agents transported by these aerosols to be administered in a targeted manner to only defined, diseased regions of the lungs. On the one hand, the dose of the pharmaceutical active agent to be administered can be reduced by this means, and on the other hand undesirable side effects on the surrounding healthy tissue can be reduced or avoided.

To achieve this aim, the problem emerges that the natural or "normal" spreading of the inhaled aerosols (e.g. in the bronchial tree or alveolar region) would have to be influenced if administration to other regions is desired in order to be able to achieve a directed spreading into such defined regions of the lung. In this connection, various mechanisms for directed supply of aerosol into the lung have been proposed in the prior art, such as, for example, described by Ernst, N. et al. (Interaction of liposomal and polycationic transfection complexes with pulmonary surfactant. *J Gene Med* 1, 331-40. (1999)) and Rosenecker, J. et al. (Interaction of bronchoalveolar lavage fluid with polyplexes and lipoplexes: analysing the role of proteins and glycoproteins. *J Gene Med* 5, 49-60. (2003)). Thus, for example, changes in the particle size in combination with various breathing techniques, e.g. long holding of breath or also an extremely slow inhalation of aerosols, have been proposed. The individual respiratory tract geometry of the patient has likewise been taken into account. For certain active agents, e.g. for a DNA transfer in the context of gene therapy, the use of viral or liposomal vectors in epithelial cells of the respiratory tract for treatment of mucoviscidosis has furthermore been described (Rudolph, C. et al. Nonviral gene delivery to the lung with copolymer-protected and transferrin-modified polyethylenimine. *Biochim Biophys Acta* 1573, 75-83. (2002)).

Ally et al. (Journal of Magnetism and Magnetic Materials 293, 442-449 (2005)), describe hypothetically the possibility of a magnet-guided transportation of aerosol particles. For this, guiding of chemotherapeutic active agents with the aid of a magnetic field into regions of the lung affected by lung cancer is proposed. However, the studies are based only on an in vitro model in which solid carbonyl-iron particles having a diameter of from 1 to 3 μm are used in air. The particle speed of v=0.34 m/s used here in combination with the magnetic field strength of 36 mT for the stated particle size of from 1 to 3 μm is coordinated to the in vitro studies described, however, and cannot be applied to the deviating in vivo conditions. Studies of the present invention have shown that under the conditions chosen by Ally et al. (2005, supra), only a very inadequate transportation of particles takes place in vivo. in vivo conditions which do not arise in an in vitro system, such as impeding of the transportation of aerosol by physiological conditions, enzymes, mucous membranes, structure and construction of the respiratory tract etc., moreover are not taken into account by Ally et al. (2005, supra). In other words, effective transportation of particles in vivo, such as is required in aerosol therapy, cannot be achieved with the parameters stated in Ally et al. (2005, supra).

Summarizing, it is to be said that none of the procedures described in the prior art has led to targeted transportation and directed deposition of aerosol particles and therefore of pharmaceutical active agents in defined regions of the lung being ensured. This has the disadvantage that increased amounts of pharmaceutical active agents must be administered in order to achieve the intended action in the diseased tissue to be treated in the lung, which as a result leads to increased active agent costs and consequently also to increased therapy costs. A further serious disadvantage is that the aerosols loaded with active agent not only are deposited in diseased regions of the respiratory tract or lung, but are also deposited in regions which are not affected by the disease, i.e. in healthy tissue. This deposition pattern is a disadvantage, since undesirable side effects may occur on non-diseased tissue of the respiratory tract or lungs due to contact with or uptake of the active agent administered. These considerations illustrate that novel methods which render possible a directed local deposition of aerosols in the respiratory tract and in particular in the lung are required.

The object of the present invention is to provide a system by which a directed in vivo transportation of aerosols into defined regions of the respiratory tract and of the lung is ensured.

This object is achieved by the subject matter of claim 1 of the present invention. Advantageous embodiments of the invention are described in the further claims.

The present invention relates in first subject matter to an aerosol containing magnetic particles, wherein the aerosol contains magnetic particles having a diameter of at least 5 nm and at most 800 nm and at least one pharmaceutical active agent. Preferably, the magnetic particles contained therein have a diameter of at least 50 nm and at most 750 nm, further preferably of at least 100 nm and at most 700 nm, more preferably of at least 150 nm and at most 600 nm, still more preferably of at least 200 nm and at most 500 nm, particularly preferably of at least 250 nm and at most 450 nm, most preferably of at least 300 nm and at most 400 nm.

The invention is based on studies with which it was possible to demonstrate for the first time that an inhaled aerosol according to the invention containing magnetic particles which contains a pharmaceutical active agent can be transported in a directed, i.e. targeted, manner into defined regions of the lung. The transportation of this aerosol according to the invention containing magnetic particles into defined regions of the lung takes place via an externally applied magnetic field which causes deposition of the magnetic particles and consequently also of the aerosol on the surface of the desired region of the lung. The present invention therefore provides an effective aerosol which can be used in vivo for directed transportation of active agent in aerosol therapy. In this connection, the term "in vivo" means any use of the aerosol according to the invention containing magnetic particles on the body of a living multi-cell organism, preferably a mammal, more preferably a human. In contrast to this, in this connection "in vitro" means any use of the aerosol according to the invention containing magnetic particles outside such a body or organism.

The magnetic particles contained in the aerosol according to the invention containing magnetic particles can consist of various metals and oxides or hydroxides thereof or contain these. Magnetic particles which are suitable according to the invention are described, for example, in the international patent application WO 02/000870, the disclosure content of which in this respect is subject matter of the present invention. The term "magnetic particles" means magnetically reacting solid phases. These solid phases are typically particles or aggregates thereof having a diameter in the nano- to micrometer range of not larger than 800 nm, and conventionally contain one or more metals or oxides or hydroxides thereof which react to the magnetic force of a magnetic field and are preferably attracted or accelerated in a defined direction by the source of the magnetic field. Temporarily magnetic particles, for example of ferrimagnetic or, preferably, ferromagnetic materials, are likewise included. Particles of paramagnetic or superparamagnetic material are furthermore included in the present invention. Suitable materials of the magnetic particles include, for example, iron, cobalt or nickel, magnetic iron oxides or hydroxides, such as $Fe_3O_4$, gamma-$Fe_2O_3$, or double oxides or hydroxides of di- or trivalent iron ions with other di- or trivalent metal ions, e.g. $Co^{2+}$, $Mn^{2+}$, $Cu^{2+}$, $Ni^{2+}$, $Cr^{3+}$, $Gd^{3+}$, $Dy^{3+}$ or $Sm^{3+}$, and any mixtures of such oxides or hydroxides. Preparation processes for magnetic particles are described e.g. in Schwertmann U. and Cornell R. M., Iron Oxides in the Laboratory, VCH Weinheim 1991, in WO 02/000870 and in DE 196 24 426.

The magnetic particles contained in the aerosol according to the invention containing magnetic particles are typically synthetic magnetic particles, i.e. are not obtainable from a biological source (a living organism). Preferably, the magnetic particles or aggregates thereof induce no systemic toxic side effects in the organism to which they are administered. According to one embodiment of the invention, the magnetic particles contained in the aerosol according to the invention containing magnetic particles are coupled to any vectors, liposomes, hollow colloids or nanoparticles described herein or to the pharmaceutical active agent(s) itself/themselves. The magnetic particles of the present invention contained in the aerosol according to the invention containing magnetic particles can be present in non-coated or coated form. If the magnetic particles are present in coated form, the coating is preferably selected from positively or negatively charged electrolytes, such as phosphates, citrates or amines, with silanes, fatty acids or polymers, e.g. polysaccharides, proteins or natural or synthetic polymers. Such a coating of the magnetic particles contained in the aerosol according to the invention containing magnetic particles serves, for example, for reduction of any toxicity of the magnetic particles, for coupling of the pharmaceutical active agent(s) to the magnetic particles, for improving/increasing the passage (of the active agent, optionally together with the magnetic particle (s)) through membranes, etc. Examples of such coatings are described, inter alia, in U.S. Pat. Nos. 4,554,088, 4,554,089, 4,208,294, 4,101,435 and DE 196 24 426, the disclosure content of which in this respect is included in full in the present invention. These coatings and the compounds used for them can have reactive functional groups as described in the following. However, these reactive functional groups can also be introduced as required by conventional chemical modifications after the coating operation. Such functional groups can have cation exchange properties, such as, for example, xanthate, xanthide, dicarboxyl, carboxymethyl, sulfonate, sulfate, triacetate, phosphonate, phosphate, citrate, tartrate, carboxylate or lactate groups of natural or synthetic polymers, such as polysaccharides, polyvinyl alcohol (PVA), polyvinylpyrrolidone (PVP) or polyethylene glycol (PEG). These functional groups can be incorporated e.g. into the natural or synthetic polymers described above before or after the coating of the magnetic particles.

As already described above, the directed transportation of the aerosol according to the invention containing magnetic particles, i.e. the transportation of the magnetic particles and active agent(s), takes place via an externally applied magnetic field, with which the inhaled magnetic particles and the pharmaceutical active agent(s) are guided into the defined regions of the respiratory tract, preferably the lung. A "magnetic field" which is suitable in the context of the invention relates to a magnetic field which is generated by a magnet as the source and, depending on the form and field strength, is capable of attracting the magnetic particles according to the invention together with active agent(s) against other physical phenomena acting on these. Such other phenomena can be, for example, the diffusion, sedimentation and/or impaction processes described above. Suitable magnetic field for the in vivo uses according to the invention should preferably generate a field strength of at least 100 mT (millitesla), preferably of at least 200 mT, likewise preferably of at least 500 mT, furthermore preferably of at least 1 T (tesla) and more. The magnetic field gradient generated by the magnetic fields should preferably be greater than 1 T/m, more preferably greater than 10 T/m. A "magnet" in the context of the present invention which generates such magnetic fields described above can be any magnet suitable for this. For example, permanent magnets or electromagnets (operated by electric current) can be employed in the context of the present invention. The intensity (the field strength of the magnet) is typically controlled via suitable measurement and control instruments connected to the magnet.

According to a preferred embodiment, the externally applied magnetic field is permanently present, i.e. after administration the aerosol according to the invention containing magnetic particles can be deflected at any point in time out of the flow line track caused by the in- and exhalation and deposited on the surface of the respiratory tract, as long as the magnetic particles contained therein arrive in a region of the magnetic field strength which is sufficient for this. Such a permanent magnetic field can be generated by any of the magnets described here, and preferably has the general properties of a magnetic field as described above. Preferably, the permanent magnetic field is active for at least the period of the treatment, i.e. of the administration or inhalation of the aerosol according to the invention containing magnetic particles.

According to another preferred embodiment, the externally applied magnetic field is not permanently present, and is active preferably only for a part of the period of treatment, i.e.

a part of the period of administration or inhalation of the aerosol according to the invention containing magnetic particles. More preferably, the magnetic field is active only during the period of the resting phases between inhalation and exhalation or between exhalation and inhalation. Such a non-permanent activation of the magnetic field preferably ensures deposition of the aerosol according to the invention containing magnetic particles on the surface during these resting phases and therefore renders possible a uniform distribution of the aerosol according to the invention containing magnetic particles. According to a particularly preferred embodiment, the control of the magnetic field can take place dynamically in coordination with the breathing of the patient as a function of the breathing rhythm of the patient, so that during the in- and exhalation by the patient no magnetic field is applied in the region to be treated, but in the resting phases a magnetic field is applied there and only then does a deposition of the aerosol according to the invention containing magnetic particles on the surface of the respiratory tract take place. Preferably, for this the air above the chosen surface of the respiratory tract is saturated by the aerosol according to the invention containing magnetic particles such that within several activations of the magnetic field(s) by the magnet(s) a significant deposition of the transported active agent or of the aerosol according to the invention containing magnetic particles on the chosen surface of the respiratory tract is rendered possible. Control of the magnet can be rendered possible, for example, by an electric circuit which triggers a signal in the nebulizer or inhaler at the start and end of the inhalation or exhalation of the patient, by which in turn the magnetic field of a magnet as described here is switched on or off. The switching on or off of the magnetic field can take place e.g. by mechanical removal or turning away of the poles of the magnet in the case of permanent magnets, and likewise mechanically in the case of electromagnets, but preferably e.g. by switching on or off of the electric current required for generation of the magnetic field.

According to a further preferred embodiment, the externally applied magnetic field is a pulsating magnetic field. A "pulsating magnetic field" in the present case means in particular that the field strength of the magnetic field decreases or increases in the region to be treated, conventionally periodically or virtually periodically. In this context, the maximum desired field strength is reached in the maximum of the pulse, while in the minimum of the pulse preferably a lowest possible field strength, more preferably a field strength less than 20%, still more preferably a field strength less than 10% of the previously applied field strength, and still further preferably no field strength is applied. Particularly preferably, the pulsating magnetic field is coordinated dynamically with the breathing of the patient as a function of the breathing rhythm of the patient such that the maximum of the pulse lies in a resting phase between inhalation and exhalation or between exhalation and inhalation, while the minimum of the pulse lies during the inhalation or exhalation. In this context, the pulsating magnetic field can have the "profile" of a rectangular pulse, a sinusoidal pulse etc., or approximations of these profiles. The pulse can be effected here, as above, by switching on or off of the magnetic field, e.g. by mechanical removal or turning away of the poles of the magnet in the case of permanent magnets, and likewise mechanically in the case of electromagnets, but preferably e.g. by switching on or off of the electric current required for generation of the magnetic field. The pulsating magnetic field can furthermore be generated with direct current or with alternating current if an electromagnet is used. If an electromagnet is operated with direct current, a magnetic field which does not change its direction (+/− poling) is preferably generated. In this context, the magnetic field formed can be adjusted by a person skilled in the art as required, according to the poling (+/− or −/+ poling).

According to a further preferred embodiment, the externally applied magnetic field is an oscillating magnetic field. In the context of the present invention, the term "oscillating magnetic field" is to be understood as meaning a magnetic field which periodically changes its direction (+/− poling). Such an oscillating magnetic field is typically generated by using an electromagnet and operating the electromagnet with alternating current. A change in the direction of the magnetic field (i.e. change in the +/− poling) effected by an oscillating magnetic field can preferably exert kinetic energy on the magnetic particles, under the influence of which the transportation of the aerosol according to the invention containing magnetic particles and/or, for example, the release of the pharmaceutical active agent coupled to the magnetic particles in the aerosol according to the invention containing magnetic particles is promoted, effected or accelerated. An oscillating magnetic field can be permanently present, or, as described above, can be matched to the breathing rhythm of the patient such that during the in- and exhalation by the patient, no oscillating magnetic field is applied in the region to be treated, but an oscillating magnetic field is applied there in the resting phases.

All the embodiments described above can also be combined with one another in a suitable manner. Thus, for example, a pulsating magnetic field can be operated in oscillation (pulsating oscillating magnetic field), i.e. the magnetic field has a characteristic pulse (e.g. rectangular or sinusoidal pulse) which, for example, oscillates in its maximum or has an oscillating course from the maximum to the minimum which constantly decreases in field strength etc.

The directed transportation of the aerosol according to the invention containing magnetic particles, i.e. the transportation of the magnetic particles and active agent(s), takes place by means of an externally arranged magnet, i.e. outside the organism to be treated (mammal, preferably human). The directed transportation into defined regions of the respiratory tract, e.g. the lung, takes place after inhalation of the aerosol according to the invention containing magnetic particles by the organism to be treated (mammal, preferably human) preferably via corresponding change(s) in position of the external magnets to the defined regions. Accordingly, it is advantageous if the magnet is freely movable. Freely movable means, for example, that the magnet can be led/moved manually. However, it is also possible and advantageous for the magnet to be attached movably to a device, e.g. a frame, on which its position can be changed, in particular can be swivelled, adjusted in height and locked, manually, electronically or by computer control. In this connection, a further possibility for positioning the external magnet(s) is arrangement of several magnets, e.g. by an arrangement of permanent magnets or electromagnets, in a row/in rows or as a bow or as a "sandwich" construction, these magnets preferably covering the region to be treated. The magnets can be activated either successively or simultaneously. By such an arrangement of several magnets e.g. a larger region can be selected for deposition of the aerosol according to the invention containing magnetic particles and therefore of the region to be treated.

The speed of the magnetic particles and pharmaceutical active agents of the aerosol according to the invention containing magnetic particles in the lung required for an effective directed transportation depends on several factors, for example on the regions of the lung into which the inhaled aerosol is to be transported, on the diameter of the magnetic particles, on the size of the pharmaceutical active agent component(s), the individual respiratory tract geometry of the organism treated etc. The speed can therefore be influenced, for example, by the diameter of the magnetic particles, the size of the active agent, the breathing technique, e.g. fast or slow inhalation, deep or shallow breathing, holding of the inhaled breath, and the field strength applied to the external magnet(s), or a magnetic field applied in oscillation and/or pulsation, as described above. For example, a cause of the increase of a deposition of particles with increasing respiratory minute volume is the resultant increasing inspiration flow (flow on inhalation). An end-inspiratory (taking place at the end of the exhalation) breath-holding time also leads to an increase in the deposition of aerosol. In the speed (of the aerosol according to the invention containing magnetic particles and of the magnetic particles and pharmaceutical active agents according to the invention contained therein), a distinction is to be made between the speed with which the aerosol according to the invention containing magnetic particles is administered, i.e. nebulized (and inhaled), and the speed with which the aerosol moves into the respiratory tract after administration. The speed with which the aerosol moves into the respiratory tract after administration is determined in particular by physiological factors, such as, for example, the respiratory tract geometry, e.g. the diameter of the respiratory tract of the patient to be treated, and is e.g. typically about 4.7 m/s at the second branching of the respiratory tract. The speed with which the aerosol and therefore the magnetic particles and pharmaceutical active agents of the invention is/are administered should advantageously be at least 3 m/s, preferably at least 5 m/s, more preferably at least 8 m/s, still more preferably at least 10 m/s, in order to ensure effective transportation of the aerosol according to the invention containing magnetic particles in vivo. The person skilled in the art will be able to define the particular suitable speed for administration of the aerosol according to the invention containing magnetic particles taking into account the abovementioned factors.

In addition to the magnetic particles, the aerosol according to the invention containing magnetic particles contains at least one pharmaceutical active agent. According to the present invention, a "pharmaceutical active agent" is to be understood as meaning any (conventional and novel) medicinal substance which is suitable for treatment of a disease of the respiratory tract or lung. "Conventional medicinal substances" are to be understood as meaning in particular so-called "small drug" medicinal substances, i.e. low molecular weight medicinal substances. Examples of these are, without being limited thereto, salbutamol, formoterol, ipatropium bromide, budesonide, fenoterol, terbutaline, tiotropium bromide, salmeterol, beclometasone, fluticasone, mometasone, ciclesonide, sodium cromoglicate, nedocromil disodium, tobramycin, theophylline, gentamycin, paclitaxel and camptothecin. "Novel medicinal substances" are to be understood as meaning in particular higher molecular weight-medicinal substances such as, for example, cytostatics, peptides, proteins or nucleic acids, and broncholytics, antibiotics, antidiabetics and immunomodulators. In this connection, the peptides and proteins can be, for example, dornase $\alpha$, insulin, $\alpha_1$-antitrypsin, catalase; superoxide dismutase, interleukin-2, surfactant proteins, secretory leukoprotease inhibitor, interferon-$\gamma$, IL-1R, anti-IgE Mab (monoclonal antibody), calcitonin, parathormone, somatropin, interferon-$\beta$, LH-RH analogues, ribavirin, interferon-$\alpha$, rh-G-CSF, erythropoietin, heparin, 1-deaminocysteine-8-D-arginine-vasopressin, ricin vaccine and cyclosporin. The nucleic acids described above are preferably those nucleic acids which code the abovementioned peptides or proteins. The nucleic acids are preferably DNA, preferably natural or synthetic DNA, cDNA, genomic DNA, naked DNA, single-stranded DNA, double-stranded DNA or circular DNA, or RNA, preferably mRNA, likewise preferably RNAi, which are not subject to any limitations in their length.

The pharmaceutical active agent contained in the aerosol according to the invention containing magnetic particles likewise includes any cytostatics which are suitable for treatment of diseases of the respiratory tract and/or lungs. In the present case, "cytostatics" are to be understood as meaning above all those compounds which have a toxic action on endogenous cells in a general manner, and inhibit cell growth in this way. Chemotherapeutics against lung cancer diseases are to be mentioned here in particular. A distinction is made between cytostatics of various groups, depending on their action mechanism. By way of example, the following e.g. are also included here:

Alkylating and crosslinking cytostatics which damage DNA. Examples of these are cyclophosphamide, N-nitroso compounds, such as carmustine, ethyleneimine (aziridine) derivatives, such as thiotepa, methanesulfates, such as busulfan, platinum complexes, such as cisplatin, procarbazine and others;

Cytostatic antibiotics, for example anthracyclines, such as daunorubicin, doxorubicin, bleomycin and mitomycins. The latter intercalate in DNA and inhibit topoisomerases;

Antimetabolites, which displace natural metabolism units. Examples are folic acid antagonists, such as methotrexate, nucleoside analogues, such as mercaptopurine, fluorouracil and others; and Hormones and hormone antagonists. These are employed in particular on tumours of hormone-dependent growth. Examples are (anti)oestrogens, such as formestane, gestagens and antiandrogens.

The pharmaceutical active agents of the aerosols of the present invention containing magnetic particles can be present in a preformulated manner, for example packed in suitable agents for transportation of pharmaceutical active agents, so-called "drug delivery" systems, for example in nanoparticles, vectors, preferably gene transfer vectors, viral or non-viral vectors, poly- or lipoplex vectors, liposomes or in a hollow colloid (i.e. hollow beads of colloidal dimensions). However, they can also be naked nucleic acids, in particular naked DNA. Suitable vectors, liposomes, hollow colloids or nanoparticles and processes for the introduction of substances, such as the pharmaceutical active agents according to the invention, into such vectors, liposomes, hollow colloids or nanoparticles are generally well-known in the prior art and are described, for example, in Cryan S-A. (Carrier-based Strategies for Targeting Protein and Peptide Drugs to the Lungs, AAPS Journal. 2005; 07(01): E20-E41) and in Sambrook et al. Molecular Cloning A Laboratory Manual, Cold Spring Harbor Laboratory (1989) NY. Gene transfer vectors which can be used are, preferably, polyethylenimines or cationic lipids, such as e.g. DOTAP. Liposomes can preferably be used for packing of cytostatics (e.g. dilauroylphosphatidylcholines); a detailed description is given, for example, in Koshkina, N. V. et al. (Paclitaxel liposome aerosol treatment induces inhibition of pulmonary metastases in murine renal carcinoma model. *Clinical Cancer Research* 7, 3258-3262 (2001)). Proteins as pharmaceutical active agents can preferably be packed into biocompatible poly-lactic/glycollic acid polymers (PLGA) by means of supercritical liquids, emulsion processes and spray drying.

The pharmaceutical active agents of the aerosol according to the invention containing magnetic particles can likewise be coated with a magnetic layer. The material of such a magnetic layer preferably consists of or comprises one of the materials described above for magnetic particles. Processes for such coatings are known in the prior art and belong to general technical knowledge.

The pharmaceutical active agents of the aerosol of the present invention containing magnetic particles can be present in a form coupled to or adsorbed on the magnetic particles or not coupled to or adsorbed on these. In the case of coupling or adsorption of the pharmaceutical active agent(s) to the magnetic particles, the coupling can be physical or chemical in nature or can be based on biological interaction. Such coupling or adsorption includes e.g. electrostatic, hydrophobic or hydrophilic interactions, van der Waals interactions, hydrogen bridge bonds and covalent bonds. Preferred covalent bonds are, for example, amide, ester, thioester, ether, thioether and disulfide bonds. All combinations of the interactions mentioned are likewise included. The coupling between the magnetic particles and pharmaceutical active agent in the aerosol according to the invention containing magnetic particles can be established, for example, by a reaction, e.g. a chemical coupling, of functional groups of the coating of the magnetic particle, as described above, and functional groups of a vector described here. Alternatively, the coupling can also be established by using a (homo- or hetero-bifunctional) linker. Such suitable homo- or hetero-bifunctional linkers are commercially obtainable. Processes which can be used for a (chemical) coupling of magnetic particles and pharmaceutical active agents of the present invention, e.g. using linkers or functional groups as described above, are well-known in the prior art and are described in detail, for example, in Bioconjugate Techniques, by Greg T. Hermanson Academic Press (1 Jan. 1996).

If the components of the aerosol according to the invention containing magnetic particles, i.e. magnetic particles and pharmaceutical active agent(s), are present in coupled form, these can be present both in combination with a solvent according to the invention and without such a solvent. In the former case, according to the present invention the aerosols containing magnetic particles are liquid aerosols, and in the latter case they are dry aerosols. An aerosol according to the invention containing magnetic particles in which magnetic particles and pharmaceutical active agent(s) are present in coupled from in combination with a solvent as described in the following is particularly preferred.

The components of the aerosol according to the invention containing magnetic particles, i.e. the magnetic particle contained therein and the pharmaceutical active agent, can also be present in the non-coupled form in the aerosol according to the invention containing magnetic particles. In order to render possible a directed deposition of the active agent in such an aerosol according to the invention containing magnetic particles, a solvent such as is described in the following is preferably employed together with the magnetic particle and the pharmaceutical active agent. According to the invention, these are then also liquid aerosols here. In this case, the transportation is by means of the drop of liquid in which both (the) magnetic particle(s) and (the) pharmaceutical active agent(s) are contained, only the magnetic particles contained therein rendering possible directed transportation and targeted deposition of the active agent. Such drops of liquid are typically obtained by a nebulizer or an equivalent device, as described below for the preparation of (liquid) aerosols according to the invention. An aerosol according to the invention containing magnetic particles in which magnetic particles and pharmaceutical active agent(s) are present in non-coupled form, in combination with a solvent as described in the following, is therefore likewise particularly preferred.

A solvent which can be used for an aerosol according to the invention containing magnetic particles can be an inorganic or organic solvent. Preferred solvents are ethanol, water and glycerine (glycerol) or mixtures thereof. Solvents which are suitable according to the present invention should preferably be tolerated well physiologically by the organism (mammal, preferably human) to which the aerosol is administered, i.e. should trigger no side effects, e.g. toxic side effects. Distilled water is a particularly preferred solvent. Ethanol-water mixtures are likewise preferred; in this case, the percentage content by weight of ethanol in these mixtures is preferably in a range of between 5% and 99% of ethanol, likewise preferably in the range of from 10% to 96% of ethanol, more preferably between 50% and 92%, most preferably between 69% and 91% of ethanol.

The preparation of a solvent-containing aerosol according to the invention containing magnetic particles with a pharmaceutical active agent which is not coupled to the magnetic particles can be carried out, for example, by preparation of drops of liquid comprising a solvent described above and magnetic particles contained therein and a pharmaceutical active agent (called formulation according to the invention in the following). For this, the components mentioned are mixed and the drops of liquid are generated, for example, with a nebulizer (see below) or an equivalent device. If the pharmaceutical active agent is coupled to the magnetic particles, this is carried out before mixing of the components mentioned, and therefore also before generation of the drops of liquid from the formulation according to the invention.

The preparation of aerosols according to the invention containing magnetic particles without a solvent can be carried out by mixing the magnetic particle and pharmaceutical active agent components. If appropriate, for this the pharmaceutical active agent is coupled to the magnetic particles beforehand and a treatment with a suitable nebulizer, a propellant gas nebulizer (see below) or an equivalent device is subsequently carried out. However, the preparation of the aerosols according to the invention can likewise be carried out by any suitable process from the prior art.

The present invention also provides a pharmaceutical composition which comprises an aerosol according to the invention containing magnetic particles, and optionally suitable auxiliary substances and/or additives. The pharmaceutical composition preferably furthermore comprises at least one (further) solvent, at least one complexing agent and/or at least one pharmaceutically acceptable acid.

In connection with the pharmaceutical composition according to the invention, "auxiliary substances and/or additives" according to the invention is to be understood as meaning any pharmacologically acceptable and therapeutically appropriate substance which is not a pharmaceutical active agent but can be formulated in the pharmaceutical composition together with the pharmaceutical active agent in order to influence, in particular to improve, qualitative properties of the pharmaceutical composition. Preferably, the auxiliary substances and/or additives display no pharmacological action or, with respect to the intended therapy, no noticeable or at least no undesirable pharmacological action. Suitable auxiliary substances and additives are, for example, pharmacologically harmless salts, for example sodium chloride, flavour substances, vitamins, e.g. vitamin A or vitamin E, tocopherols or similar vitamins or provitamins which occur in the human organism, antioxidants, such as, for example, ascorbic acid, and stabilizers and/or preservatives for prolonging the use life and storage life of the pharmaceutical composition, and other conventional auxiliary substances and additives known in the prior art.

Preservatives can be employed, for example, in the pharmaceutical composition according to the invention in order to protect the pharmaceutical composition from contamination with pathogenic germs. Suitable preservatives are, in particular, benzalkonium chloride or benzoic acid or benzoates, such as sodium benzoate, in the concentrations known from the prior art. The amount of, for example, benzalkonium chloride added is preferably approximately 1 mg to 50 mg per 100 ml, more preferably approximately 7 mg to 15 mg per 100 ml, still more preferably approximately 9 mg to 12 mg per 100 ml of the pharmaceutical composition according to the invention. However, pharmaceutical compositions according to the invention which contain no preservatives are particularly preferred.

At least one (further) "solvent" of the pharmaceutical composition according to the invention is to be understood as meaning the solvents described above in connection with the aerosol according to the invention containing magnetic particles. If liquid aerosols according to the invention containing magnetic particles are employed in this context in the pharmaceutical composition according to the invention, the at least one (further) "solvent" is at least one solvent in addition to that contained in the liquid aerosol. In liquid aerosols according to the invention containing magnetic particles, the at least one (further) "solvent" is accordingly at least one "solvent". The at least one (further) "solvent" contained in the pharmaceutical composition according to the invention can comprise one solvent or any combination of the solvents described above.

In connection with the pharmaceutical composition according to the invention, "complexing agents" are to be understood as meaning molecules which are suitable for entering into complex bonds. Preferably, cations, particularly preferably metallic cations, are complexed according to the invention by these compounds. Preferred complexing agents are edetic acid (EDTA, ethylenediaminetetraacetate) or a known salt thereof, e.g. sodium EDTA or disodium EDTA. Preferably, sodium edetate (ethylenediaminetetraacetic acid disodium salt), optionally in the form of its hydrates, particularly preferably in the form of its dihydrate, is employed. The concentration of the complexing agents employed is preferably in a range of from approximately 1 mg to 100 mg per 100 ml, more preferably in a range of from approximately 5 mg to 50 mg per 100 ml, more preferably from approximately 6 mg to 30 mg per 100 ml, most preferably from approximately 7 mg to 20 mg per 100 ml of the pharmaceutical composition according to the invention.

Pharmaceutically acceptable inorganic or organic acids are used, in particular, to adjust the pH of the pharmaceutical composition according to the invention, this pH preferably being in a range of from approximately 3.0 to approximately 8.5, preferably between 3.5 and 6.0, particularly preferably between 4.0 and 7.0. The pH is very particularly preferably about 7.0. Pharmaceutically acceptable inorganic or organic acids can in principle be selected from all suitable acids or bases. In connection with the pharmaceutical composition according to the invention, examples of preferred (pharmaceutically acceptable) inorganic acids can be selected from the group consisting of hydrochloric acid, hydrobromic acid, nitric acid, sulfuric acid and phosphoric acid, hydrochloric acid and sulfuric acid being preferred in particular. In connection with the pharmaceutical composition according to the invention, examples of particularly suitable (pharmaceutically acceptable) organic acids can be selected from the group consisting of malic acid, tartaric acid, maleic acid, succinic acid, acetic acid, formic acid and propionic acid, and particularly preferably ascorbic acid, fumaric acid and citric acid. Mixtures of the acids mentioned can optionally also be employed, in particular of acids which, in addition to their acidification properties, also have other properties, e.g. in use as flavour substances or antioxidants, such as, for example, citric acid or ascorbic acid.

For exact adjustment of the pH described above for the pharmaceutical composition according to the invention, pharmaceutically acceptable bases can furthermore optionally also be employed. Suitable bases in this connection are alkali metal hydroxides, alkali metal carbonates and alkali metal ions, preferably sodium. It is to be ensured that the salts resulting from such bases, which are then contained in the pharmaceutical composition according to the invention, are pharmaceutically acceptable with the above-mentioned acid(s). The combination of the particular suitable acids and bases for adjustment of the pH of the pharmaceutical composition according to the invention can be varied as required and according to the requirements of the composition to be prepared. A corresponding choice or combination of such acids and bases as described above can easily be made by a person skilled in the art.

The preparation of a pharmaceutical composition according to the invention can be carried out analogously to the preparation described above for the aerosols according to the invention. Further components optionally contained in the pharmaceutical composition according to the invention, i.e. auxiliary substances and/or additives, the solvent preferably contained therein, complexing agents and/or at least one pharmaceutically acceptable acid, can be added in the aerosol preparation process described above by processes known in the prior art. Alternatively, the pharmaceutical composition according to the invention can be achieved by any process known in the prior art.

The dosage of the components described above in the pharmaceutical composition according to the invention is subject to various factors, for example the nature of the treatment, the disease, the condition of the organism (mammal, preferably human), the age of the sick organism to which the pharmaceutical composition according to the invention is administered, the nature of the active agent etc. Such parameters are known to the person skilled in the art and the determination of the dosages is subject to his general technical knowledge.

The aerosol according to the invention containing magnetic particles and the pharmaceutical composition according to the invention serve in particular for nasal or oral administration. A preferred embodiment therefore relates to an aerosol according to the invention containing magnetic particles or a pharmaceutical composition according to the invention for nasal or oral administration. The administration is preferably carried out via a nebulizer. A further preferred embodiment therefore relates to an aerosol according to the invention containing magnetic particles or a pharmaceutical composition according to the invention for administration via a nebulizer.

A "nebulizer" in the context of the present invention is any standard nebulizer suitable for medicinal aerosols. The term "nebulizer" is to be understood as being synonymous with the term "inhaler". Nebulizers are conventionally used to prepare and to administer liquid and/or dry aerosols according to the invention containing magnetic particles, e.g. based on solvents (as already described above). For this, the formulations according to the invention are conventionally fed to a nebulizer in order to prepare from this the preferably propellant gas-free aerosols according to the invention containing magnetic particles. For this, the nebulizer typically sprays a defined volume of the formulation using high pressures through small jets, in order to generate an inhalable aerosol according to the invention containing magnetic particles in this way. Nebulizers which are particularly suitable here are those which can nebulize a small amount of a liquid formulation according to the invention in the therapeutically necessary dosage within a few seconds into an aerosol suitable for therapeutic inhalation. Such nebulizers are suitable in particular for propellant gas-free administration of the (liquid) aerosols according to the invention containing magnetic particles or pharmaceutical compositions according to the invention. Such a nebulizer is described e.g. in the international patent applications WO 91/14468 and WO 97/12687. In such a nebulizer, a medicament solution is converted by means of a high pressure of up to 600 bar into a medicinal aerosol which is suitable for administration to the respiratory tract and lung and is sprayed. A specific jet such as is described, for example, in WO 94/07607 or WO 99/16530, is used for nebulizing such a solution.

Suitable nebulizers for nasal or oral administration of the dry aerosols according to the invention containing magnetic particles, i.e. aerosols according to the invention containing magnetic particles without a solvent, are typically inhalation apparatuses or nebulizers driven by propellant gas. Propellant gases here can be, for example, CFCs or HFCs. In this respect, reference is made to the publication "Theorie und Praxis der Inhalationstherapie [Theory and Practice of Inhalation Therapy], pages 31 to 70, Arcis Verlag (2000), in which a detailed description of nebulizers which can be used and methods of use thereof is/are disclosed.

Further examples of suitable nebulizers for nasal or oral administration of the aerosols according to the invention containing magnetic particles are jet nebulizers driven by compressed air (e.g. PARI LC plus, PARI GmbH, Starnberg, Germany), Venturi jet nebulizers, jet nebulizers driven by water vapour or ultrasound nebulizers (e.g. AeronebLab, Aerogen, Inc., Stierlin Court, Canada; eFLOW, PARI GmbH, Starnberg, Germany). Nebulizers of a size which can be carried by the patient (human), e.g. the Respimat@, as described in WO 97/12687, are likewise suitable. A detailed description of suitable nebulizers is also to be found in "Theorie und Praxis der Inhalationstherapie [Theory and Practice of Inhalation Therapy]", pages 31 to 70, Arcis Verlag (2000).

The present invention therefore also additionally provides a device for nebulizing and/or administration of the aerosol according to the invention containing magnetic particles, comprising a nebulizer as described above filled with an aerosol according to the invention containing magnetic particles. The device according to the invention can be configured as a device having a replaceable reservoir of aerosol according to the invention containing magnetic particles. Alternatively, the device according to the invention can be a disposable device. The device according to the invention can furthermore be mobile or stationary. If the device according to the invention is mobile, the weight is preferably not more than 2 kg, particularly preferably not more than 1 kg, still more preferably not more than 500 g. If the device according to the invention is stationary in configuration, the device preferably comprises a replaceable reservoir of aerosol according to the invention containing magnetic particles.

The present invention also provides the use of an aerosol according to the invention containing magnetic particles or of a pharmaceutical composition according to the invention for prophylaxis and/or therapy of diseases of the respiratory tract and/or lungs, in particular inflammatory and/or obstructive diseases of the respiratory tract and/or lungs, for example melanomas or malignant melanomas of the respiratory tract, in particular the lung, lung cancer, lung tumours, lung carcinomas, small cell lung carcinomas, throat cancer, bronchial carcinomas, larynx cancer, head/neck tumours, tongue cancer, sarcomas and blastomas in the region or vicinity of the respiratory tract, in particular the lung, as well as asthma and COPD (chronic obstructive pulmonary disease), lung emphysema, chronic bronchitis, pneumonia and hereditary diseases, for example mucoviscidosis, human surfactant protein B deficiency and $\alpha_1$-antitrypsin deficiency, and for therapy after a lung transplant and for pulmonary vaccination and for anti-infective therapy of the lung (in cases of bacterial (e.g. *Bronchiolitis obliterans*) or viral colonization of the lung).

The present invention also provides the use of an aerosol according to the invention containing magnetic particles or optionally of a pharmaceutical composition according to the invention for the preparation of a medicament or a device for prophylaxis and/or therapy of diseases of the respiratory tract and/or lungs, in particular inflammatory and/or obstructive diseases of the respiratory tract and/or lungs, for example melanomas or malignant melanomas of the respiratory tract, in particular the lung, lung cancer, lung tumours, lung carcinomas, small cell lung carcinomas, throat cancer, bronchial carcinomas, larynx cancer, head/neck tumours, tongue cancer, sarcomas and blastomas in the region or vicinity of the respiratory tract, in particular the lung, as well as asthma, COPD, lung emphysema, chronic bronchitis, pneumonia and hereditary diseases, for example mucoviscidosis, human surfactant protein B deficiency and $\alpha_1$-antitrypsin deficiency, and for therapy after a lung transplant and for pulmonary vaccination and for anti-infective therapy of the lung (in cases of bacterial (e.g. *Bronchiolitis obliterans*) or viral colonization of the lung).

The present invention also provides the use of an aerosol according to the invention containing magnetic particles or of a pharmaceutical composition according to the invention in diagnostics. The present invention alternatively provides the use of an aerosol according to the invention containing magnetic particles or of a pharmaceutical composition according to the invention for the production of a device in diagnostics. For example, the diagnostic agent can be a contrast medium, including e.g. iodine-containing (water-soluble) x-ray-positive contrast media; iodine-containing (water-insoluble) x-ray-positive contrast media; barium containing (water-insoluble) x-ray-positive contrast media; x-ray-negative contrast media; gadolinium compounds, such as e.g. gadolinium DTPA; technetium compounds, such as e.g. compounds containing technetium-99m, for example phosphonates labelled with technetium-99m, Tc-99m-MDP=Tc-99m-methylene-diphosphonate, Tc-99m-tetrofosmin; superparamagnetic iron oxide particles as described above; contrast media which can pass through membranes; enzyme-specific NMR probes, e.g. with paramagnetic dinuclear complexes with lanthanoid ions based on cyclic polyaminopolyacetic acids; glucose contrast media, for example for use in PET (positron emission tomography), including e.g. glucose contrast media coupled to a labelled substance which renders possible external location, e.g. using isotopes which emit positrons, e.g. $^{18}$-fluorine, such as, for example, fluoro-2-deoxy-2-D-glucose labelled with $^{18}$-fluorine (18FDG), etc. The diagnostic agent can furthermore comprise peptides, proteins, nucleic acids, antibodies, in particular detectable antibodies, low molecular weight detectable compounds, etc. For diagnostics, the aerosol according to the invention containing magnetic particles or a pharmaceutical composition according to the invention can be introduced by the directed transportation described into defined regions of the respiratory tract, in particular the lung, and can function as a diagnostic agent in these regions. By this means, structural changes to the lung which indicate a pathological change can be detected and imaged early on, and therefore facilitate the diagnosis of a potential disease. Such a diagnostic agent can be used in particular for imaging lung tumours or lung emphysemas (imaging MRI, CT, determination of the extent of a lung emphysema).

A preferred embodiment of the present invention relates to the use of an aerosol according to the invention containing magnetic particles or of a pharmaceutical composition according to the invention for directed deposition of aerosol in the respiratory tract or in the lung of an organism (mammal, preferably human) and the use of an aerosol according to the invention containing magnetic particles or of a pharmaceutical composition according to the invention preferably for nasal or oral administration, preferably via a nebulizer.

The present invention also provides a method for inhalatory use of an aerosol according to the invention containing magnetic particles or of a pharmaceutical composition according to the invention, wherein the method comprises the preparation of an aerosol according to the invention containing magnetic particles or of a pharmaceutical composition according to the invention and the administration of this to an organism (mammal, preferably human). The preparation and administration are preferably carried out as described above.

Preferably, the method for inhalatory use of an aerosol according to the invention containing magnetic particles is carried out using a magnetic field which is applied externally as described above and is permanently, or still more preferably is not permanently active. Particularly preferably, during the administration the externally applied magnetic field is active only during the period of the resting phases between inhalation and exhalation or between exhalation and inhalation. Still more preferably, the guiding of the magnetic field can take place dynamically in coordination with the breathing of the patient as a function of the breathing rhythm of the patient, so that during the in- and exhalation of the patient, no magnetic field is applied in the region to be treated, but in the resting phases a magnetic field is applied there and only then does a deposition of the aerosol according to the invention containing magnetic particles on the surface of the respiratory tract take place. Preferably, for this the air above the chosen surface of the respiratory tract is saturated by administration of the aerosol according to the invention containing magnetic particles such that within several activations of the magnetic field(s) by the magnet(s) a significant deposition of the transported active agent or of the aerosol according to the invention containing magnetic particles on the chosen surface of the respiratory tract is rendered possible. Control of the magnet can be rendered possible, for example, by an electric circuit which triggers a signal in the nebulizer or inhaler at the start and end of the inhalation or exhalation by the patient, by which in turn the magnetic field of a magnet as described here is switched on or off.

The present invention also provides a kit comprising an aerosol according to the invention containing magnetic particles or a pharmaceutical composition according to the invention, an external magnet which generates a magnetic field and a nebulizer.

All the references given in the description of the present invention are included in their full scope in the present invention. The invention is explained in more detail in the following with the aid of figures and examples. It is not intended to limit the present invention to these.

BRIEF DESCRIPTIOON OF THE DRAWINGS

Figure 2:
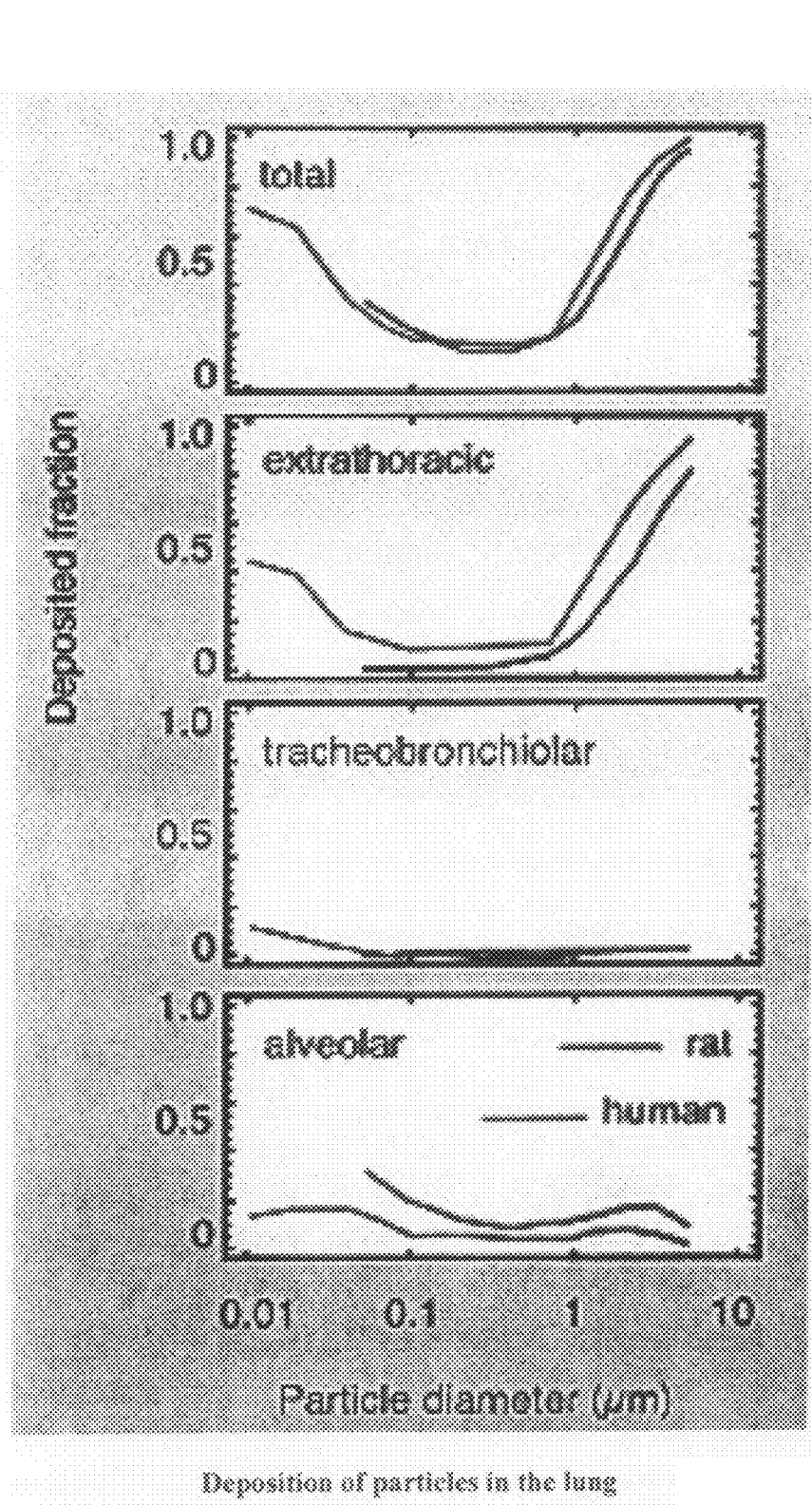

FIG. 1 shows the various mechanisms of deposition of aerosol particles in the lung. The hypothetical deposition on the inner wall of the air cavity (respiratory tract epithelium) of various particles is shown as a function of their diameter and the consequent deposition mechanism FIG. 2 shows the normal local deposition of aerosol particles in the lung during calm nasal breathing as a function of their diameter. Studies with respect to local deposition have shown that the particle diameter has a decisive influence on local deposition.

It can be seen from FIG. 2 that inhaled particles having a diameter of between 0.1 to 1 μm overall are deposited only minimally in the lung. On the other hand, the deposition of particles of larger and smaller diameter increases overall. It can likewise be seen from FIG. 2 that particles having a diameter of 0.01 μm are deposited to the extent of approx. 80% and of 5 μm are deposited to the extent of approx. 100%. The increasing deposition of larger particles is to be attributed above all to the increasing deposition by sedimentation and impaction as the particle size increases. In contrast, the deposition of small particles of <0.1 μm increases due to deposition by diffusion. The total deposition during calm nasal breathing is comparable in rats and in humans.

Figure 15:
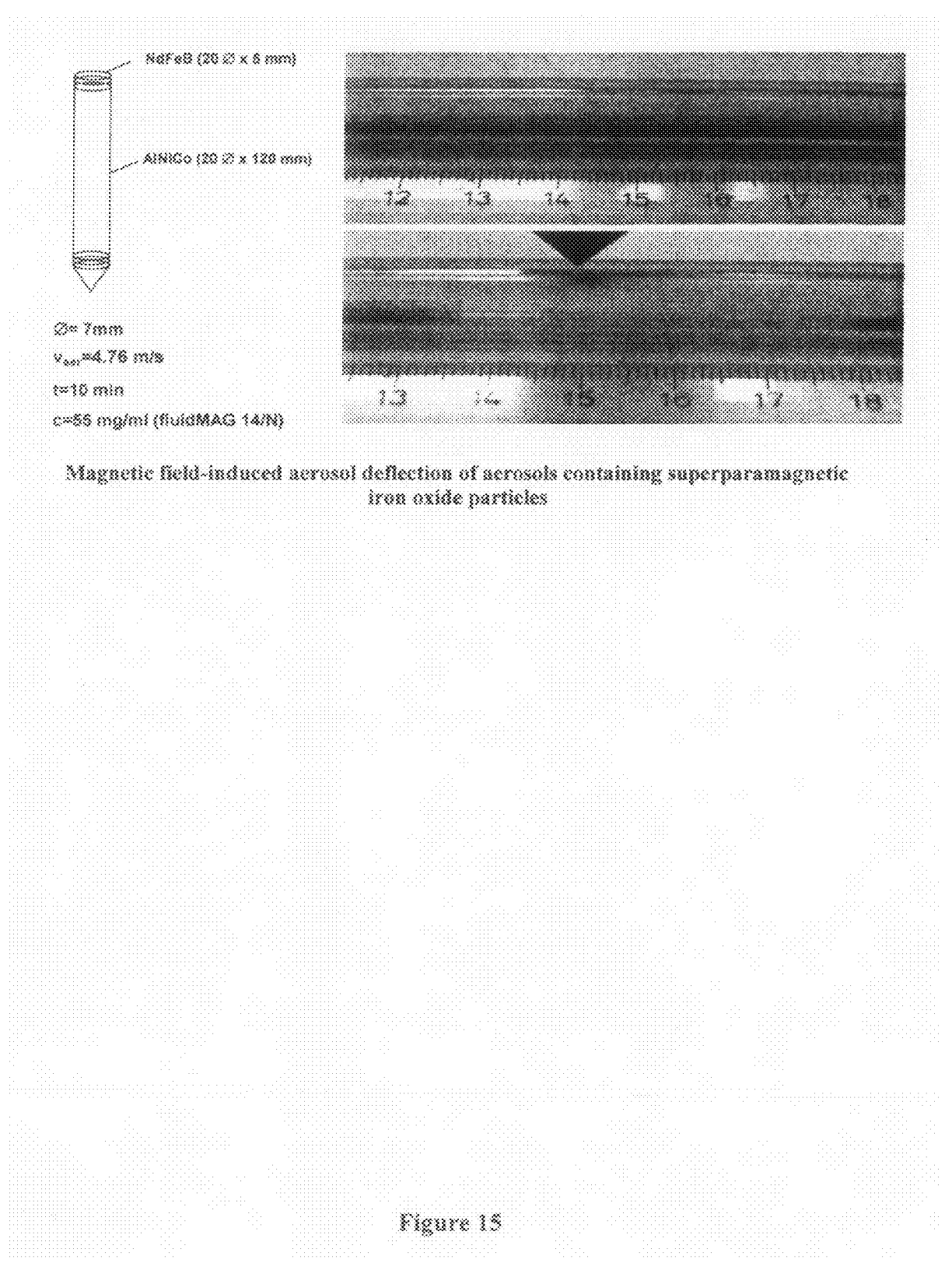

It has been found, according to the invention, that it was possible to increase considerably the deposition of particles by the magnetic field-guided deposition according to the invention (see also FIG. 15).

With respect to the local deposition of the particles, FIG. 2 shows that this also depends greatly on the particle diameter. Extrathoracic deposition takes place chiefly in the nose and is only slightly lower than the total deposition. In particular, particles having a diameter larger than 1 μm or smaller than 0.05 μm are already filtered in the nose. The remaining proportion of the inhaled aerosol is mostly deposited in the alveolar region. The aerosol proportion deposited in the tracheobronchial region (trachea and respiratory tract) is relatively low, and reaches up to 15% for very small particles, while particles of >3 μm are deposited to the extent of only 1 to 3%. In the alveolar region, approx. 15% of the inhaled dose of particles of diameter of <0.1 μm is deposited. For particles having a diameter of from 0.1 to 3 μm, the proportion deposited varies between 5 to 10%. Deposition is almost negligible for particles of >5 μM. Overall, it can be said that tracheobronchial deposition is very similar between rats and humans (see Schulz, H. & Muhle, H. 323-345 (Academic Press, 2000)).

Figure 3:
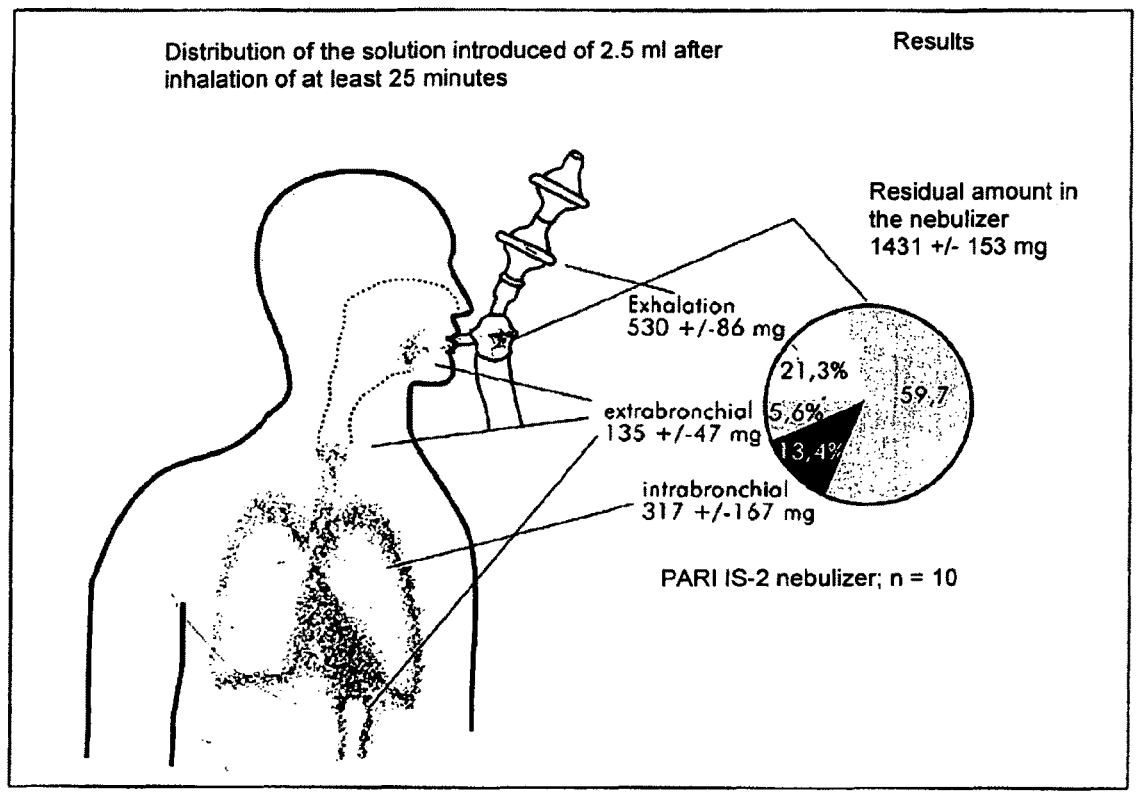

According to the invention, it has been found (see also FIG. 9) that by the magnetic field-guided deposition according to the invention, the deposition of magnetic particles can be effected and also increased in a targeted manner in regions in which normally only a low deposition takes place, as described above, for example, for the tracheobronchial and the alveolar region FIG. 3 shows the deposition of particles using a modern jet nebulizer operated with compressed air (PARI IS-2). Of a total inhaled aerosol dose (exhalation, extrabronchial and intrabronchial), 52% is exhaled again (see Köhler, D. & Fischer, F. *Theorie und Praxis der Inhalationstherapie [Theory and Practice of Inhalation Therapy]* (Arcis Verlag GmbH, Munich, 2000). These results illustrate that a large proportion of the inhaled aerosol dose is exhaled again. This exhaled proportion is minimized considerably with the present invention by the magnetic field-guided deposition of aerosol. It can be seen from FIG. 3 that in total only 33% of the inhaled dose is deposited in the lung. The results from experiments of the invention (shown in FIGS. 5 and 6) show that an approx. 2.2- to 2.5-fold increase in this inhaled dose is deposited when the influence according to the invention of an external magnetic field is present. Since in the abovementioned experiments the breathing conditions with and without a magnetic field were identical, on application of the results to the data from FIG. 3 it emerges that the aerosol dose deposited in the lung can be increased from 33% to approx. 82.5% with the aerosols according to the invention.

FIG. 4 shows the deposition pattern of conventionally administered aerosols using inhalation methods which correspond to the prior art. As can be seen, the inhaled aerosol is distributed homogeneously throughout the entire lung. A directed guiding of the aerosol into defined regions of the lung is not possible with the methods known hitherto.

Figure 5:
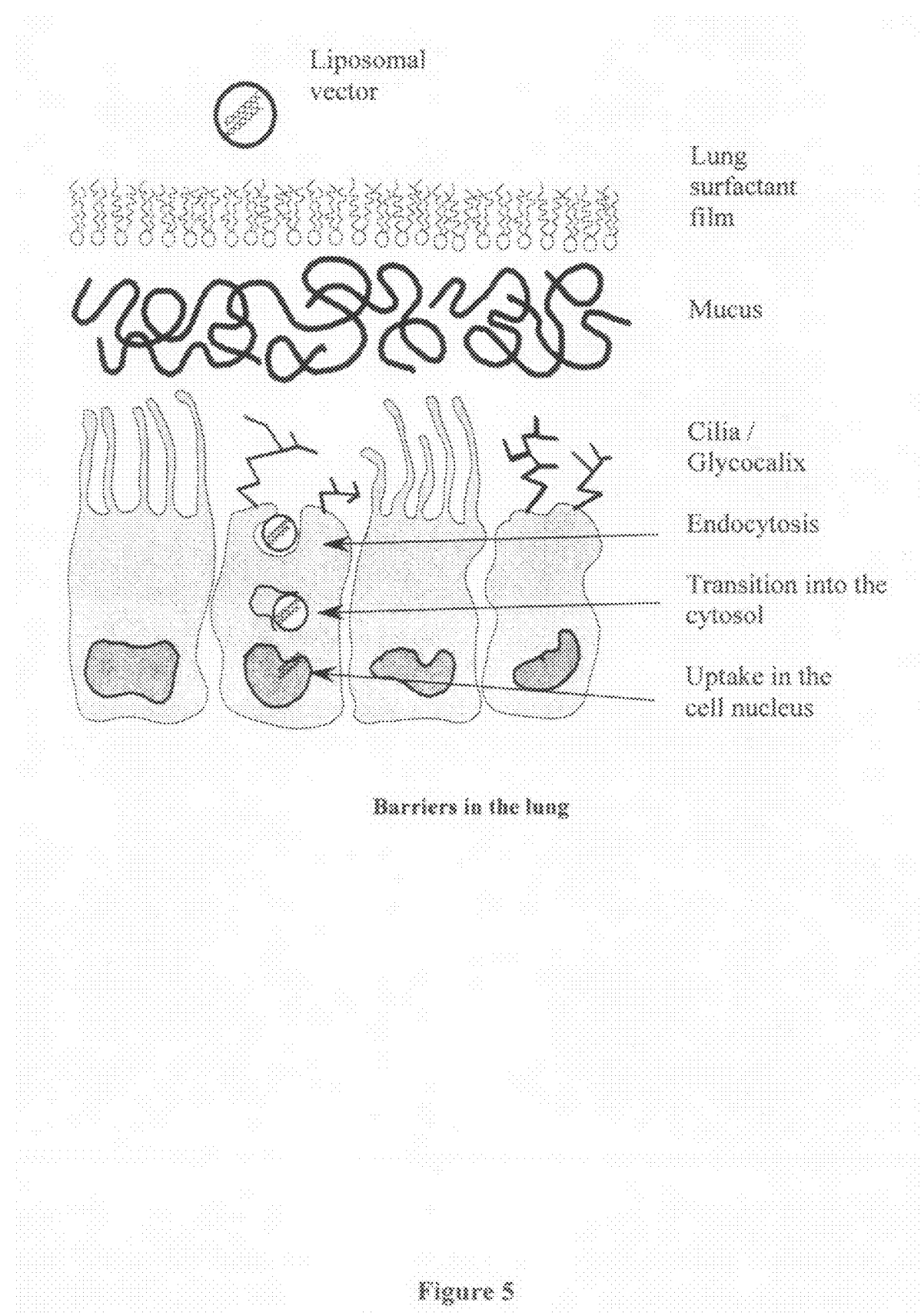

FIG. 5 shows a diagram of a cross-section through the mucus layer and the respiratory epithelium. This figure gives an overview of conditions of in vivo transfer of pharmaceutical active agents (and magnetic particles) of the present invention. After topical application of, for example, gene vectors via the respiratory tract, extracellular and intracellular barriers are to be overcome before the DNA enters into the cell nucleus. The lung surfactant film, mucus layer, proteins contained therein, such as e.g. nucleases (DNase), form a first barrier in this context. Further physical barriers are the cilia and glycocalix of the cell surface. After intracellular uptake of gene vectors, the DNA must be protected from lysosomal degradation and transported to the cell nucleus. The cell nucleus pores of the nucleus membrane are a further obstacle to successful transportation. The mucus layer per se is a barrier which is difficult to penetrate. Diffusion of particles of >500 nm through the mucus layer therefore virtually stops (see Sanders, N. N., De Smedt, S. C. & Demeester, J. The physical properties of biogels and their permeability for macromolecular drugs and colloidal drug carriers [Review]. *Journal of Pharmaceutical Sciences* 89, 835-849 (2000)).

Figure 6:
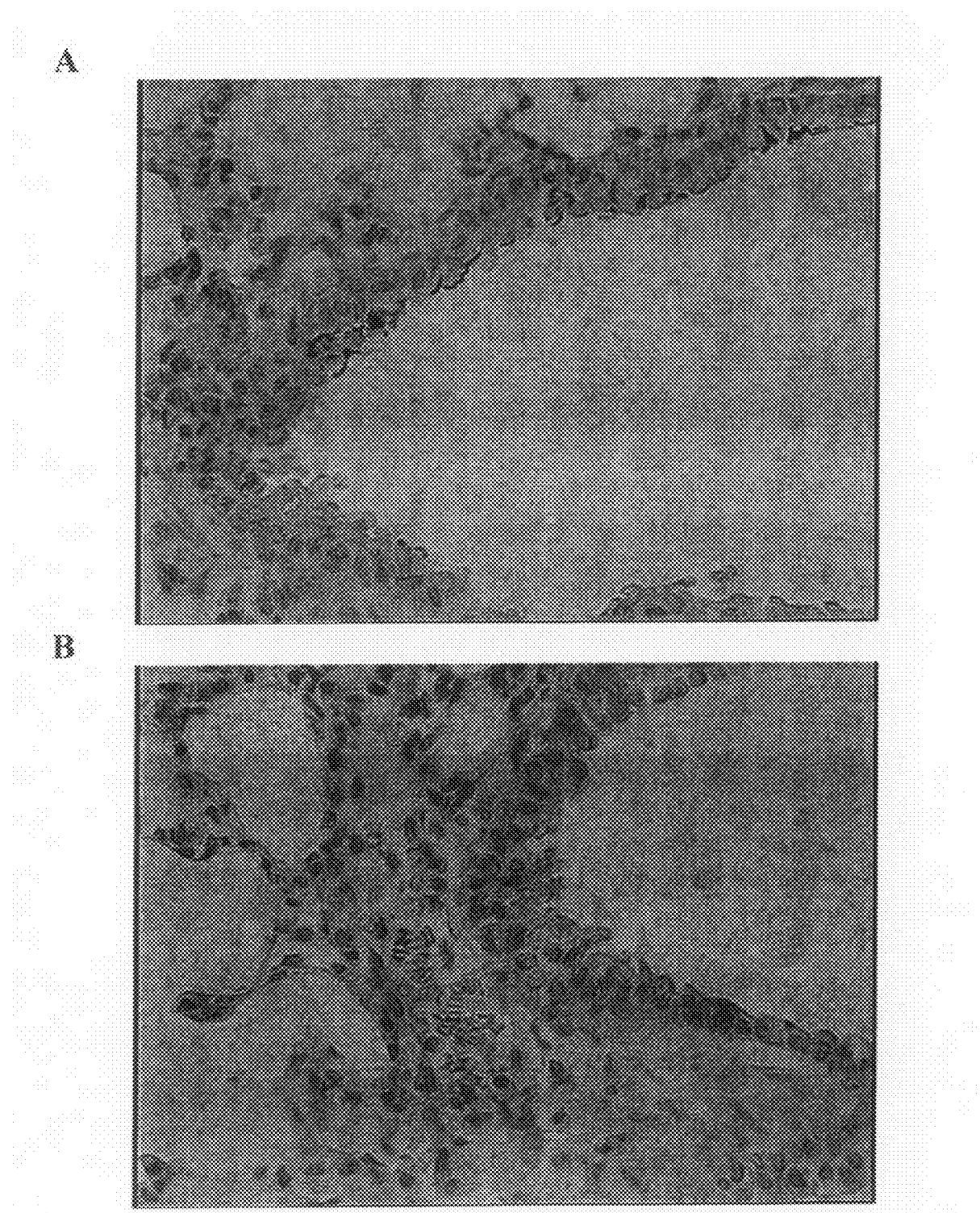

FIG. 6 shows the cells of the lung lying underneath the mucus layer (as shown in the cross-section from FIG. 5). FIG. 6A shows the cells after administration of an aerosol according to the invention containing magnetic particles under the influence of a magnetic field, FIG. 6B shows the cells after administration of the corresponding aerosol according to the invention containing magnetic particles without the influence of a magnetic field. As can be seen in FIG. 6A, the magnetic particles adhere to the cell surface and they are to be seen as black deposits. On the other hand, no deposits are detectable on the cell surface in FIG. 6B. With this study result it was possible to demonstrate that the aerosols according to the invention containing magnetic particles or the magnetic particles and pharmaceutical active agents (which are either coupled to the magnetic particles or contained with them in a drop of liquid, as described above) contained therein are transported in a directed manner through the mucus layer, whereas this is not the case without the application according to the invention of an external magnetic field.

FIG. 7 shows a diagram of the concept according to the invention of the magnetic field-guided administration of aerosol. An aerosol according to the invention containing magnetic particles is generated with a commercially obtainable nebulizer (PARI, Starnberg, Germany). The drops of liquid containing magnetic particles formed here are inhaled by the patient and guided by the externally applied magnetic field directly into the desired regions of the lung of the patient.

FIG. 8 shows a diagram of an animal study on mice of the concept according to the invention of the magnetic field-guided administration of aerosol. Aerosols containing magnetic particles were guided in a targeted manner into defined regions of the lung of a mouse under the influence of an applied magnetic field.

FIG. 9 shows the study set-up of an animal study on mice of the concept according to the invention of the magnetic field-guided administration of aerosol. In the mouse model, the thorax of the mice was opened, so that on the one hand it was possible to expose and intubate the trachea, and on the other hand it was possible to apply an external magnetic field to a defined region of the lung. The mouse was respirated (the flexiVent system from SCIREQ is shown) during administration of the aerosol, and the aerosol was introduced through a connected nebulizer into the respiration system (symbolized by the red arrow). The nebulizer was synchronized with the respiration frequency, so that aerosol was administered into the mouse lung only during inspiration.

The general study set-up of the intubated mouse connected to the respirator and the nebulizer is shown in FIG. 9A. In FIG. 9B, the intubated mouse is shown, fixed under the electromagnet, which was used as the external magnetic field. The intubated mouse with the opened thorax (without the magnet) can be seen in FIG. 9C. FIG. 9D shows the iron tip (pole shoe) of the electromagnet placed on the right mouse lung. The mouse was fixed under the electromagnet during administration of the aerosol such that the iron tip of the electromagnet did not come into contact with the left mouse lung. The precise course of the study is disclosed in Example 1.

FIG. 10 shows the histological evaluation of an animal study on mice of the magnetic field-guided aerosol administration according to the invention. The distribution of superparamagnetic iron oxide nanoparticles after administration of aerosol into the lung tissue of a mouse is shown. A magnetic field was applied to the right lung during administration of the aerosol. The superparamagnetic iron oxide nanoparticles appear as a brown colouration and can be seen in FIG. 10 as dark regions in the image.

Longitudinal sections through the mouse lung are shown in the first row of FIG. 10. The pointwise accumulation of the superparamagnetic iron oxide nanoparticles at the position of the pole shoe of the electromagnet can be clearly seen (left-hand image). In contrast, no pointwise accumulation of the superparamagnetic iron oxide nanoparticles is to be seen in the left lung, but a homogeneous and diffuse distribution of the superparamagnetic iron oxide particles over the lung (middle image). A control lung in which as expected no brown colouration of the lung is to be observed is also shown (right-hand image). In all the control lungs of FIG. 10, no superparamagnetic iron oxide nanoparticles were administered as an aerosol.

The second row of FIG. 10 shows marked sections from the lung sections of the first row in magnification. The accumulation of the superparamagnetic iron oxide nanoparticles induced in the right mouse lung by the magnetic field can be clearly seen (left-hand image), while this is not observed in the left mouse lung (middle image). Control lungs in which as expected no accumulation of superparamagnetic iron oxide nanoparticles is to be observed are likewise shown (right-hand images).

In the third and fourth row of FIG. 10, marked sections of the enlargements of the second row are shown in turn. A clear accumulation of the superparamagnetic iron oxide nanoparticles in the lung is to be seen only in the regions in which the pole shoe of the electromagnet was placed (left-hand images). Control lungs in which as expected no accumulation of superparamagnetic iron oxide nanoparticles is to be observed are likewise shown (right-hand images).

These results shown in FIG. 10 illustrate that it is possible to guide an aerosol according to the invention containing magnetic particles successfully in a controlled manner into defined regions of the lung by means of externally applied magnetic fields. The invention therefore represents a substantial step in the direction of a completely novel technology for administration of aerosol and for targeted therapy of numerous diseases of the respiratory tract and/or lungs.

FIG. 11 shows the quantitative evaluation of an animal study on mice of the magnetic field-guided aerosol administration according to the invention. In this study, the thorax of the mouse was opened and an electromagnet was placed on the right lung. In FIG. 11, the results of the left lung (without a magnetic field applied) are compared with those of the right lung (with a magnetic field applied).

In FIG. 11, the amount of the quantity of superparamagnetic iron oxide nanoparticles deposited in the lungs of the mouse under the influence of a magnetic field applied only to the right mouse lung is shown. Aerosol administration of superparamagnetic iron oxide nanoparticles in the absence of a magnetic field leads to a uniform distribution between the right and left mouse lung (white columns). In contrast, application of a magnetic field to the right mouse lung causes an approx. 8-fold accumulation compared with the left mouse lung (black columns).

Viewed overall, the total deposition of superparamagnetic iron oxide nanoparticles in the mouse lung is at least 2.8 times higher under the influence of the magnetic field than in the absence of the magnetic field. According to the invention, the directed deposition of aerosols of the present invention containing magnetic particles has also been demonstrated by these studies and results.

FIG. 12 shows the quantitative evaluation of an animal study on mice of the magnetic field-guided aerosol administration according to the invention. In this study, the thorax of the mouse was closed and an electromagnet was placed on the right lung. FIG. 12 compares the results of the left lung (without a magnetic field applied) to those of the right lung (with a magnetic field applied).

The background of this study was also use in humans, where the magnetic field-guided administration of aerosol has to take place with the thorax closed. As can be seen in FIG. 12, with the thorax closed the influence of the magnetic field applied to the right lung also results in an at least 2.5-fold increase in the deposition of the superparamagnetic iron oxide nanoparticles, and therefore virtually corresponds to the results of the administration of aerosol with the thorax opened (shown in FIG. 11). It has thus been demonstrated that the present invention can be used in human aerosol therapy and under the associated conditions (closed thorax).

Figure 13:
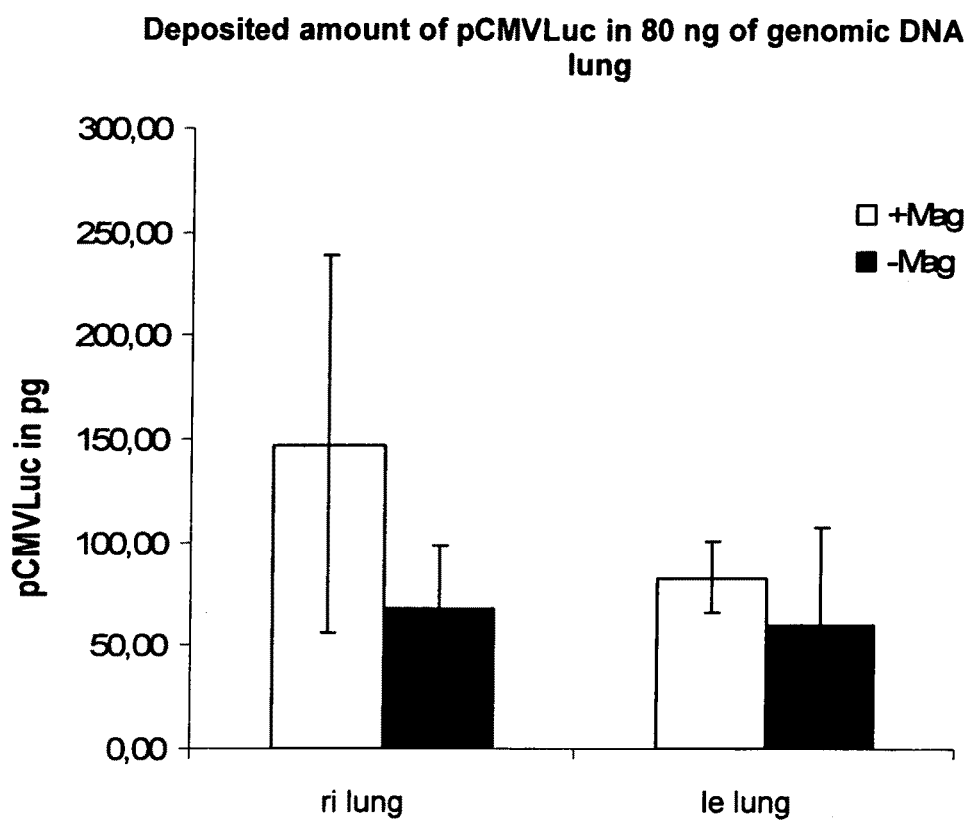

FIG. 13 shows a further quantitative evaluation of an animal study on mice of the magnetic field-guided aerosol administration according to the invention. In this study, plasmid DNA (pCMVLuc) (as the active agent) was formulated with superparamagnetic iron oxide nanoparticles and administered as an aerosol according to the invention. In this study also, the thorax of the mouse was closed and an electromagnet was placed on the right lung. FIG. 13 compares the results of the left lung (without a magnetic field applied) to those of the right lung (with a magnetic field applied).

The background of this study was also here use in humans, where the magnetic field-guided administration of aerosol has to take place with the thorax closed. As can be seen from FIG. 13, with the thorax closed the influence of the magnetic field applied to the right lung also results in an at least 2.2-fold increase in the deposition of the plasmid DNA administered, which was formulated with superparamagnetic iron oxide nanoparticles, and therefore virtually corresponds to the results of the administration of aerosol with the thorax opened (shown in FIG. 10). It has thus been demonstrated again that the present invention can be used in human aerosol therapy and under the associated conditions (closed thorax).

FIG. 14 shows a diagram of a study set-up for investigating the magnetic field-induced deflection of the aerosol.

A test model was established for magnetic field-guided pharmaceutical active agent transfer according to the invention in aerosol therapy. A diagram of the study set-up of the test model is shown in FIG. 14. The test model is characterized by the following features: A standard nebulizer (PARI LC plus; made available by the partner company PARI GmbH, Starnberg) was connected to a 60 cm long hose of plastic having an internal diameter of 0.7 cm, and various magnets were positioned on the outer wall of the hose at a distance of 30 cm from the nebulizer. The nebulizing conditions chosen correspond to the diameter and the air speed such as are to be found in the 1st-2nd bronchial branching of the human lung. Aqueous formulations according to the invention containing superparamagnetic iron oxide nanoparticles were nebulized into the hose for defined times and the magnetic field-dependent deflection efficiency was quantified by measuring the hose area containing iron oxide nanoparticles.

FIG. 15 shows the magnetic field-induced aerosol deflection of aerosols containing superparamagnetic iron oxide particles.

To illustrate the magnetic field-induced deflection of aerosols according to the invention containing iron oxide particles, the deposition of the iron oxide particles on the inner wall of the hose of the test model shown in FIG. 14 is shown by way of example in FIG. 15. In this study, a bar magnet mounted with an iron tip was used. The nebulizing parameters are stated. The deposition of aerosol in the hose without application of the magnetic field is shown as a control in the upper photo of FIG. 15. It can be clearly seen that the iron oxide particles are deposited uniformly on the base of the hose if no magnetic field is applied. In contrast, the accumulation of the iron oxide particles at the iron tip of the permanent magnet on application of the magnetic field can be clearly seen. It can likewise be clearly seen that the flight path of the aerosol particles changes as a function of the magnetic field, since no deposition of the iron particles is to be seen on the base of the hose underneath the iron tip of the magnet.

FIG. 16 shows the magnetic field-induced aerosol deflection of aerosols according to the invention containing superparamagnetic iron oxide particles.

Various magnet arrangements were investigated by means of the test model shown in FIG. 14. It emerged above all that generation of magnetic field gradients by targeted placing of pieces of iron (e.g. paper clips) in the magnetic field greatly increased the deposition of the aerosols. The most efficient arrangement was achieved by placing a permanent magnet in each case above and below the hose. The result is shown in FIG. 16.

FIG. 17 shows the further parameter of the field strength, which has an influence on the deflection properties of aerosols according to the invention containing superparamagnetic iron oxide particles. The investigations were carried out with the aid of the test model shown in FIG. 14.

It can be clearly seen that the deposition of the aerosols containing superparamagnetic iron oxide particles decreases greatly with the magnetic field strength. As expected, the greater the magnetic field, the greater the deflection of the aerosol.

FIG. 18 shows the further parameter of the magnetic particle diameter, which has an influence on the deflection properties of aerosols according to the invention containing superparamagnetic iron oxide particles. The investigations were carried out with the aid of the test model shown in FIG. 14.

It can be seen that the deposition of the aerosol depends on the size of the diameter of the superparamagnetic iron oxide particles. Interestingly, the deflection of small particles of 50 nm in diameter is entirely more effective that that of larger particles of more than 800 nm at the same iron concentration. The magnetic particles used according to the invention having a diameter of up to 800 nanometers therefore show significantly better results for transportation of aerosol than magnetic particles having a diameter larger than 800 nanometers. The aerosols according to the invention containing magnetic particles are therefore excellently suitable for use in aerosol therapy.

FIG. 19 shows the further parameter of the iron concentration, which has an influence on the deflection properties of aerosols according to the invention containing superparamagnetic iron oxide particles. The investigations were carried out with the aid of the test model shown in FIG. 14.

A further parameter which has a great influence on the deflection properties is the concentration of the nebulized superparamagnetic iron oxide particles in the aerosol solution. In FIG. 19, this is shown by way of example for particles of 100 nm in size. It can be seen that a minimum concentration of 12.5 mg/ml of solution must be used, so that the aerosols containing superparamagnetic iron oxide particles can be deflected.

FIG. 20 shows, in tables, the values of FIG. 17, parameter of field strength; FIG. 18, parameter of magnetic particle diameter; and FIG. 19, parameter of iron concentration.

Figure 21:
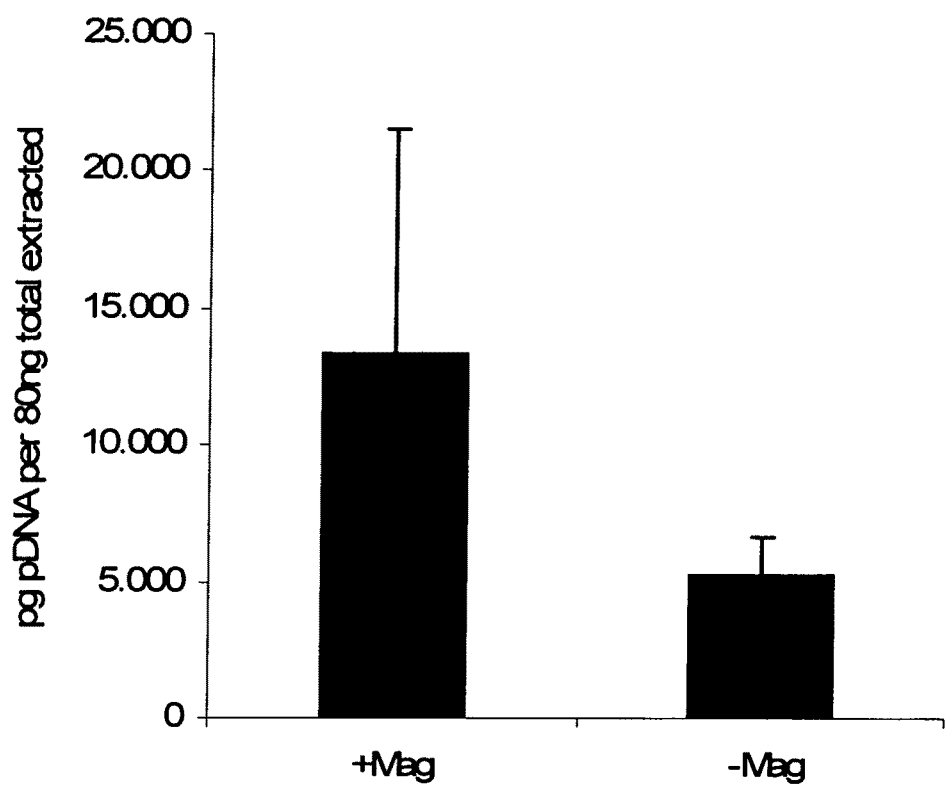

FIG. 21 describes the results of in vivo studies with BALB/c mice (see Example 4). For this, two permanent magnets were fixed on the thorax of BALB/c mice and an aerosol according to the invention containing magnetic particles was administered. 24 hours after administration of the aerosol according to the invention containing magnetic particles, the mice (n=3) were sacrificed and the amount of plasmid DNA in the lungs was determined by means of a real-time PCR. As can be seen in FIG. 21, the presence of the permanent magnets on the thorax led to a 2.5-fold higher deposition of plasmid DNA in the lung.

Figure 22:
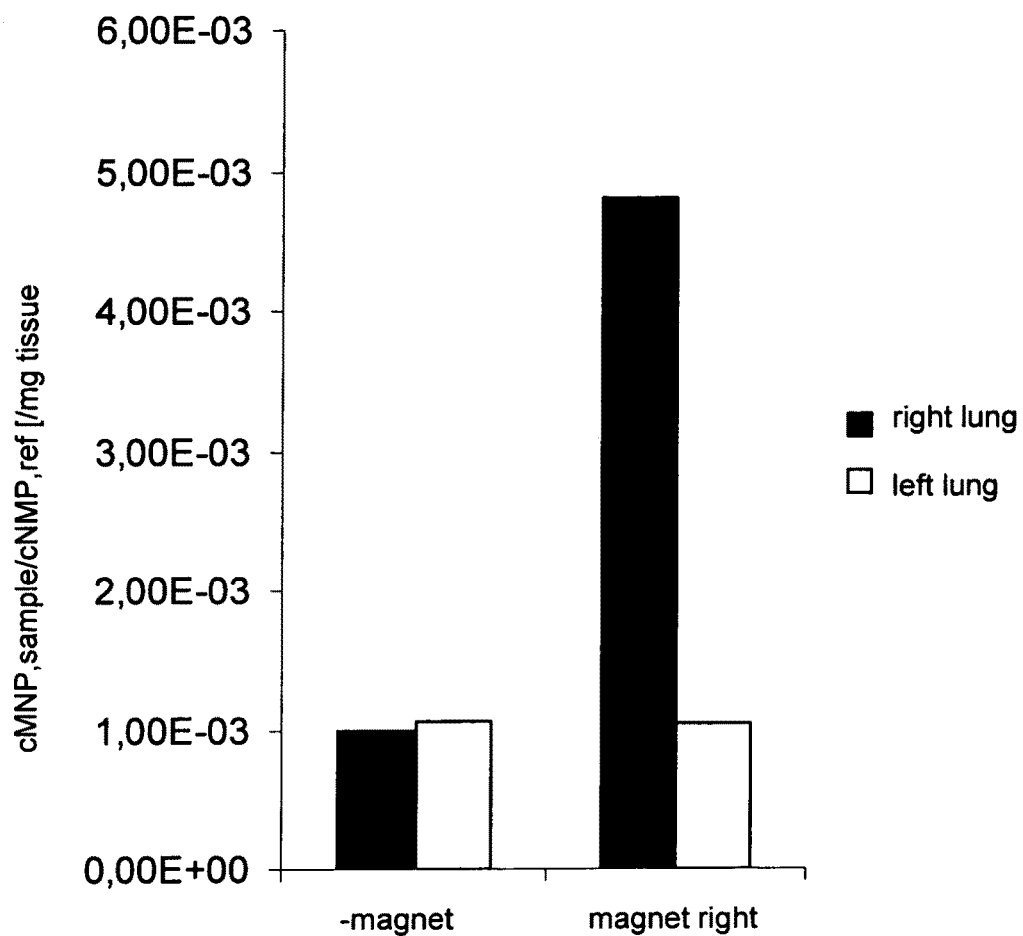

FIG. 22 describes the results of in vivo studies with anaesthetized domestic pigs (see Example 5). For this, an aerosol according to the invention containing magnetic particles was administered to two BALB/c anaesthetized domestic pigs. On the first pig, a permanent magnet was placed on the right side of the breast, and no magnet was placed on the second pig during the administration. After the administration of the aerosol, the pigs were sacrificed and the lungs removed. The magnetic particles in the ventral lung regions were quantified by means of magnetorelaxometry. As can be seen in FIG. 22, the number of magnetic particles in the right lung by means of a magnetic field is 5 times higher than without a magnetic field.

EXAMPLES

Example 1

Administration of an Aerosol According to the Invention Containing Magnetic Particles BALB/c mice were anaesthetized with an intraperitoneal injection of pentobarbital. After the corneal reflex had stopped, the animals were intubated or connected to the Flexivent system with a nebulizer via a tracheotomy. The mice were respirated under volume control with a breathing frequency of $f=120$ min$^{-1}$ and a tidal volume of TV=10 µl/g at a PEEP of 4 cm $H_2O$. Before the start of the inhalation, the lung impedance was measured as the starting value (pertubation+ snapshot).

The pole shoe (iron tip) of an electromagnet was placed over the right mouse lung and operated with a current intensity of I=10 A (1 T). 0.7 ml of an aqueous formulation according to the invention with superparamagnetic iron oxide nanoparticles (fluidMAG-PEI 50 nm, c=6.25 mg/ml) was administered in 10 s intervals (n=20, output rate=200 µl/min). At the end of the experiment, the mouse lungs were removed and the right and left mouse lung were deep-frozen in liquid nitrogen separately from one another. The content of magnetic particles in the lungs was quantified by means of magnetorelaxometry (Lange J, et al., Magnetorelaxometry, a new binding specific detection method based on magnetic nanoparticles, JOURNAL OF MAGNETISM AND MAGNETIC MATERIALS 252 (1-3): 381-383 November 2002). The study group size was 4 mice (3 mice for quantification of the magnetic particle content of the lungs by means of magnetorelaxometry and one mouse for the histological processing (cryosections)).

Example 2

Aerosol Containing Magnetic Particles with Plasmid DNA as a Pharmaceutical Active Agent Superparamagnetic iron oxide nanoparticles which are coated with the cationic polymer polyethylenimine (50 nm) (fluidMAG-PEI, Chemicell, Berlin, Germany) are diluted in distilled water to a final iron concentration of 12.5 mg/ml. The volume is 4 ml. Plasmid DNA (pCMVLuc) is diluted with distilled water to a concentration of 0.625 mg/ml (final volume 4 ml). This results in a total dose of 5 mg of DNA. The plasmid DNA solution is pipetted into the iron oxide nanoparticle solution and the components are mixed thoroughly by pipetting up and down. The resulting pH of the solution is adjusted to pH=7.0. The solution is incubated at room temperature for 10 min before administration by nebulizing. It is to be ensured that the electrolyte concentration is kept as low as possible, in order to prevent a salt-induced aggregation of the iron oxide nanoparticles. For this reason, no electrolytes but nonionic substances, such as, for example, glucose or glycerol, should be used for isotonic adjustment of solutions. The duration of the nebulizing depends on the type of nebulizer and for a PARI BOY (PARI GmbH, Starnberg, Germany) is approx. 15 min for a 4 ml volume with an ejection rate of 5-6 l/min. This results in a nebulizing time of approx. 30 min. The magnetic field applied is adjusted to a magnetic field gradient of at least 10 T/m and is placed at the desired position of the lung during the nebulizing.

Example 3

Aerosol Containing Magnetic Particles with Cytostatics as a Pharmaceutical Active Agent Doxycycline HCl is dissolved in a 20% ethanolic aqueous solution with a concentration of 16 mg/ml in a volume of 4 ml. 4 ml of a solution of superparamagnetic iron oxide nanoparticles (c=12.5 mg/ml, 50 nm, fluidMAG-PEI, Chemicell, Berlin, Germany) are pipetted into this solution. The solution is nebulized under the conditions mentioned in Example 2.

Paclitaxel is dissolved in a mixture of ethanol and polyethylene glycol 200 (PEG-200) with a concentration of 75 mg/ml in a volume of 4 ml. 4 ml of a solution of superparamagnetic iron oxide nanoparticles (c=12.5 mg/ml, 50 nm, fluidMAG-PEI, Chemicell, Berlin, Germany) are pipetted into this solution. The solution is nebulized under the conditions mentioned in Example 2.

Dilauroylphosphatidylcholine and paclitaxel are dissolved in a ratio of 10:1 (w/w) in t-butanol and the solution is frozen at −70° C. and lyophilized. The lyophilisate is stored at −20° C. until used. Before use, the lyophilisate is reconstituted with sterile distilled water and vortexed until multilamellar liposomes are formed. The final concentration of paclitaxel is 10 mg/ml in a total volume of 4 ml. 4 ml of a solution of superparamagnetic iron oxide nanoparticles (c=12.5 mg/ml, 50 nm, fluidMAG-PEI, Chemicell, Berlin, Germany) are pipetted into this solution. The solution is nebulized under the conditions mentioned in Example 2.

Example 4 in vivo Studies with BALB/c Mice

Two permanent magnets (NeoFeBr, 10×10×10 mm; 500 mT) were fixed on the thorax of BALB/c mice (Elevage Janvier, Route Des Chenes Secs, Le Genest Saint Isle, 53940 France) with tissue adhesive. The mice were placed in a Plexiglas box which was divided into six chambers of equal size of wire permeable to aerosol. A mouse with or without magnet was placed alternately in the individual chambers. For preparation of the aerosol according to the invention containing magnetic particles, plasmid DNA which codes for the luciferase gene was diluted with distilled water to a volume of 5 ml (c=0.2 mg/ml). Superparamagnetic iron oxide nanoparticles (fluidMAG-PEI, 50 nm) were then diluted with distilled water to a volume of 5 ml (c=3 mg/ml), the DNA solution was pipetted rapidly into the nanoparticle solution and the components were mixed thoroughly by pipetting up and down several times. Thereafter, the solution was administered to the mice in the Plexiglas box by means of a nebulizer. The solution is nebulized under the conditions mentioned in Example 2. The general procedure for administration of aerosol is described in the publication of Rudolph et al. (2005) (Rudolph C, Ortiz A, Schillinger U, Jauernig J, Plank C, Rosenecker J. Methodological optimization of polyethylenimine (PEI)-based gene delivery to the lungs of mice via aerosol application. J Gene Med. 2005 January; 7(1):59-66.; Rudolph C, Schillinger U, Ortiz A, Plank C, Golas M M, Sander B, Stark H, Rosenecker J., Aerosolized nanogram quantities of plasmid DNA mediate highly efficient gene delivery to mouse airway epithelium., Mol Ther. 2005 September; 12(3):493-501). 24 hours after administration of the aerosol according to the invention containing magnetic-particles, the mice (n=3) were sacrificed and the amount of plasmid DNA in the lungs was determined by means of a real-time PCR. The presence of the permanent magnets on the thorax led to a 2.5-fold higher deposition of plasmid DNA in the lung (cf. FIG. 21). These results show that permanent magnets are also suitable for accumulating medicinal substances in aerosols containing magnetic particles in the lung in vivo.

Example 5 in vivo Studies with Anaesthetized Domestic Pigs

Two anaesthetized domestic pigs (approx. 20 kg) were respirated under controlled conditions, and during the respiration an aerosol according to the invention containing magnetic particles as described in Examples 1, 2 and 3 was administered (10 ml of fluidMAG-PEI, 50 nm, 25 mg/ml). On the first pig, a permanent magnet (4 magnets 8×4×2 cm lying one above the other, 0.8 T) was placed on the right side of the breast, and no magnet was placed on the second pig during the administration. After the administration of the aerosol, the pigs were sacrificed and the lungs removed. The magnetic particles in the ventral lung regions were quantified by means of magnetorelaxometry. The number of magnetic particles in the right lung by means of a magnetic field is 5 times higher than without a magnetic field (see FIG. 22). These studies show that aerosols according to the invention containing magnetic particles can also be guided into the lung of large test animals in a targeted manner.

The invention claimed is:

1. An aerosol composition comprising two independent entities:
   (i) a first entity comprising magnetic particles,
   (ii) a second entity comprising a pharmaceutical active agent,
   wherein the magnetic particles have a diameter of at least 5 nm and at most 800 nm, wherein the two independent entities are contained in the aerosol composition without being complexed in a physical, chemical, or biological manner.

2. The aerosol composition according to claim 1, wherein the magnetic particles have a diameter of at least 50 nm and at most 750 nm.

3. The aerosol composition according to claim 1, wherein the magnetic particles and the pharmaceutical active agent are contained in a solvent.

4. The aerosol composition according to claim 3, wherein the solvent is an inorganic or organic solvent.

5. The aerosol composition according to claim 3, wherein the solvent is selected from the group consisting of ethanol, water and glycerine and mixtures thereof.

6. The aerosol composition according to claim 1, wherein the pharmaceutical active agent is selected from the group consisting of nucleic acids, peptides, proteins, cytostatics, broncholytics, antibiotics, antidiabetics and immunomoduiators.

7. The aerosol composition according to claim 1, wherein the pharmaceutical active agent is contained in a vector, liposome, hollow colloid or nanoparticle.

8. The aerosol composition according to claim 1, wherein the magnetic particles consist of metals and/or oxides and/or hydroxides thereof or contain these.

9. The aerosol composition according to claim 1, wherein the magnetic particles consist of metals selected from the group consisting of iron, cobalt or nickel, magnetic iron oxides or hydroxides, such as $Fe_3O_4$, gamma-$Fe_2O_3$, double oxides or hydroxides of di-or trivalent iron ions with other di-or trivalent metal ions, such as $Co^{2+}$, $Mn^{2+}$, $Cu^{2+}$, $Ni^{2+}$, $Cr^{3+}$, $Gd^{3+}$, $Dy^{3+}$ or $Sm^{3+}$, and any mixtures thereof.

10. The aerosol composition according to claim 1, wherein the magnetic particles consist of paramagnetic or superparamagnetic material.

11. The aerosol composition according to claim 1, wherein the aerosol is included in a pharmaceutical composition and said pharmaceutical composition further comprises suitable auxiliary substances and/or additives.

12. The aerosol composition according to claim 11, additionally comprising at least one solvent, at least one complexing agent and/or at least one pharmaceutically acceptable acid.

13. A method for prophylaxis and/or therapy of diseases of a subject's respiratory tract and/or lungs, inflammatory and/or obstructive diseases of a subject's respiratory tract and/or selected from melanomas or malignant melanomas of a subject's respiratory tract, lung, lung cancer, lung tumours, lung carcinomas, small cell lung carcinomas, throat cancer, bronchial carcinomas, larynx cancer, head/neck tumours, tongue cancer, sarcomas and blastomas in a the region or vicinity of a subject's respiratory tract, as well as asthma, COPD (chronic obstructive pulmonary disease), lung emphysema, chronic bronchitis, pneumonia and hereditary diseases, mucoviscidosis, human surfactant protein B deficiency and α1-antitrypsin deficiency, and for therapy after a lung transplant and for pulmonary vaccination and for anti-infective therapy of a subject's lung comprising administering to a subject in need thereof to transform a body from a disease state to a healthier state comprising:
   a pharmaceutically effective amount of aerosol composition comprising two independent entities:
   (i) a first entity comprising magnetic particles; and
   (ii) a second entity comprising a pharmaceutical active agent, wherein the magnetic particles have a diameter of at least 5 nm and at most 800 nm, wherein the two independent entities are contained in the aerosol composition without being complexed in a physical, chemical, or biological manner.

14. The method according to claim 13, wherein the aerosol composition is deposited by a magnetic field onto a surface of the region of the respiratory tract and/or lung to be treated.

15. The method according to claim 14, wherein the magnetic field has a field strength of at least 100 mT (millitesla), at least 200 mT, at least 500 ml or at least 1 T (tesla).

16. The method according to claim 14, wherein the magnetic field has a magnetic field gradient of greater than 1 T/m or greater than 10 T/m.

17. The method according to claim 13, wherein the magnetic field is pulsating, an oscillating or a pulsating—oscillating magnetic field.

18. The method according to claim 13, wherein the magnetic field is matched dynamically to the breathing of the patient and is active only during resting pauses between inhalation and exhalation or exhalation and inhalation.

19. A kit comprising the aerosol composition according to claim 1, and an external magnet which generates a magnetic field and a nebulizer.

20. The aerosol composition according to claim 2, wherein the magnetic particles have a diameter of at least 100 nm and at most 700nm.

21. The aerosol composition according to claim 20, wherein the magnetic particles have a diameter of at least 150 nm and at most 600 nm.

22. The aerosol composition according to claim 21, wherein the magnetic particles have a diameter of at least 200 nm and at most 500nm.

23. The aerosol composition according to claim 22, wherein the magnetic particles have a diameter of at least 250 nm and at most 450 nm.

24. The aerosol composition according to claim 23, wherein the magnetic particles have a diameter of at least 300 nm and at most 400 nm.

25. An aerosol composition comprising two independent entities:
   (i) a first entity comprising magnetic particles,
   (ii) a second entity comprising a pharmaceutical active agent,
   wherein the magnetic particles have a diameter of at least 5 nm and at most 800 nm, wherein the pharmaceutical active agent is selected from the group consisting of peptides, proteins, cytostatics, broncholytics, antibiotics, antidiabetics and immunomodulators, wherein the two independent entities are contained in the aerosol composition without being complexed in a physical, chemical, or biological manner.

26. A method for prophylaxis and/or therapy of diseases of a respiratory tract and/or lungs, inflammatory and/or obstructive diseases of the respiratory tract and/or lungs selected from melanomas or malignant melanomas of the respiratory tract, the lung, lung cancer, lung tumours, lung carcinomas, small cell lung carcinomas, throat cancer, bronchial carcinomas, larynx cancer, head/neck tumours, tongue cancer, sarcomas and blastomas in a region or vicinity of the respiratory tract, the lung, as well as asthma, COPD (chronic obstructive pulmonary disease), lung emphysema, chronic bronchitis, pneumonia and hereditary diseases, mucoviscidosis, human surfactant protein B deficiency and α1-antitrypsin deficiency, and for therapy after a lung transplant and for pulmonary vaccination and for anti-infective therapy of the lung comprising: administering a pharmaceutically effective amount of the aerosol composition of claim 1 to a subject in need thereof to transform a body from a disease state to a healthier state.

27. A method for prophylaxis and/or therapy of diseases of a respiratory tract and/or lungs, inflammatory and/or obstructive diseases of the respiratory tract and/or lungs selected from melanomas or malignant melanomas of the respiratory tract the lung, lung cancer, lung tumours, lung carcinomas, small cell lung carcinomas, throat cancer, bronchial carcinomas, larynx cancer, head/neck tumours, tongue cancer, sarcomas and blastomas in a region or vicinity of the respiratory tract, the long, as well as asthma, COPD (chronic obstructive pulmonary disease), lung emphysema, chronic bronchitis, pneumonia and hereditary diseases, mucoviscidosis, human surfactant protein B deficiency and α1-antitrypsin deficiency, and for therapy after a lung transplant and for pulmonary vaccination and for anti-infective therapy of the lung comprising: administering a pharmaceutically effective amount of the aerosol composition of claim 25 to a subject in need thereof to transform a body from a disease state to a healthier state.

28. A method for prophylaxis and/or therapy of diseases of a respiratory tract and/or lungs, inflammatory and/or obstructive diseases of the respiratory tract and/or lungs selected from melanomas or malignant melanomas of the respiratory tract, the lung, lung cancer, lung tumours, lung carcinomas, small cell lung carcinomas, throat cancer, bronchial carcinomas, larynx cancer, head/neck tumours, tongue cancer, sarcomas and blastomas in a region or vicinity of the respiratory tract, the lung, as well as asthma, COPD (chronic obstructive pulmonary disease), lung emphysema, chronic bronchitis, pneumonia and hereditary diseases, mucoviscidosis, human surfactant protein B deficiency and α1-antitrypsin deficiency, and for therapy after a lung transplant and for pulmonary vaccination and for anti-infective therapy of the lung comprising:

administering a pharmaceutically effective amount of an aerosol composition comprising two independent entities:

(iii) a first entity comprising magnetic particles, (iv) a second entity comprising a pharmaceutical active agent, wherein the magnetic particles have a diameter of at least 5 nm and at most 800 nm, wherein the pharmaceutical active agent is selected from the group consisting of peptides, proteins, cytostatics, broncolytics, antibiotics, antidiabetics and immunomodulators, wherein the two independent entities are contained in the aerosol composition without being complexed in a physical, chemical, or biological manner.

* * * * *

UNITED STATES PATENT AND TRADEMARK OFFICE
CERTIFICATE OF CORRECTION

PATENT NO. : 8,567,410 B2  
APPLICATION NO. : 11/991535  
DATED : October 29, 2013  
INVENTOR(S) : Carsten Rudolph et al.

Page 1 of 1

It is certified that error appears in the above-identified patent and that said Letters Patent is hereby corrected as shown below:

In the claims:

Claim 6, column 26, lines 53-54: please delete "immunomoduiators" and insert --immunomodulators--.

Claim 9, column 26, line 64: please delete "$Fe_3,O_4$" and insert --$Fe_3O_4$--.

Claim 12, column 27, lines 8-11: please add the word "further" after the word "one" and before the word "solvent". Claim 12 should read "…, additionally comprising at least one further solvent…".

Claim 15, column 27, line 45: please delete "500 ml" and insert --500 mT--.

Claim 27, column 28, line 46: please delete "the long" and insert --the lung--.

Signed and Sealed this  
Fifth Day of August, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,567,410 B2 | Page 1 of 1 |
| APPLICATION NO. | : 11/991535 | |
| DATED | : October 29, 2013 | |
| INVENTOR(S) | : Rudolph et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1300 days.

Signed and Sealed this
Seventh Day of April, 2015

Michelle K. Lee
*Director of the United States Patent and Trademark Office*